(12) United States Patent
Kemp et al.

(10) Patent No.: US 8,395,781 B2
(45) Date of Patent: Mar. 12, 2013

(54) AUTOMATIC CALIBRATION SYSTEMS AND METHODS OF USE

(75) Inventors: Nathaniel J. Kemp, Concord, MA (US); Badr Elmaanaoui, Billerica, MA (US); Elizabeth Begin, Billerica, MA (US)

(73) Assignee: Volcano Corporation, San Diego, CA (US)

( * ) Notice: Subject to any disclaimer, the term of this patent is extended or adjusted under 35 U.S.C. 154(b) by 0 days.

(21) Appl. No.: 13/403,471

(22) Filed: Feb. 23, 2012

(65) Prior Publication Data

US 2012/0162660 A1  Jun. 28, 2012

Related U.S. Application Data

(63) Continuation-in-part of application No. 13/243,399, filed on Sep. 23, 2011, which is a continuation of application No. 12/172,980, filed on Jul. 14, 2008, now Pat. No. 8,049,900.

(60) Provisional application No. 60/949,467, filed on Jul. 12, 2007.

(51) Int. Cl.
*G01B 9/02* (2006.01)

(52) U.S. Cl. .................................. 356/479

(58) Field of Classification Search ............... 356/243.8, 356/394, 477–483, 73.1; 600/310, 341, 476–480
See application file for complete search history.

(56) References Cited

U.S. PATENT DOCUMENTS

| | | | |
|---|---|---|---|
| 4,803,639 A | 2/1989 | Steele et al. | |
| 4,864,578 A | 9/1989 | Proffitt et al. | |
| 4,969,742 A | 11/1990 | Falk et al. | |
| 5,025,445 A | 6/1991 | Anderson et al. | |
| 5,065,010 A * | 11/1991 | Knute .................... 250/227.21 |
| 6,043,883 A | 3/2000 | Leckel et al. | |
| 6,538,778 B1 | 3/2003 | Leckel et al. | |
| 6,570,894 B2 | 5/2003 | Anderson | |
| 6,615,062 B2 * | 9/2003 | Ryan et al. .................... 600/310 |
| 6,646,745 B2 | 11/2003 | Verma et al. | |
| 6,795,188 B2 | 9/2004 | Ruck et al. | |
| 6,795,196 B2 | 9/2004 | Funakawa | |
| 6,798,522 B2 | 9/2004 | Stolte et al. | |
| 6,912,051 B2 | 6/2005 | Jensen | |
| 6,937,346 B2 | 8/2005 | Nebendahl et al. | |
| 6,937,696 B1 * | 8/2005 | Mostafavi ............... 378/95 |
| 6,947,147 B2 | 9/2005 | Motamedi et al. | |
| 6,985,234 B2 | 1/2006 | Anderson | |
| 7,027,743 B1 | 4/2006 | Tucker et al. | |
| 7,359,062 B2 | 4/2008 | Chen et al. | |
| 7,391,520 B2 | 6/2008 | Zhou et al. | |
| 7,414,779 B2 | 8/2008 | Huber et al. | |

(Continued)

FOREIGN PATENT DOCUMENTS

| | | |
|---|---|---|
| EP | 01172637 A1 | 1/2002 |
| JP | 2004004080 A | 1/2004 |

(Continued)

OTHER PUBLICATIONS

DC Adler, et al., "Phase-Sensitive Optical Coherence Tomography at up to 370,000 Lines Per Second Using Buffered Fourier Domain Mode-Locked Lasers", Optics Letters, vol. 32, No. 6, pp. 626-628, (2007). Abstract Only.

(Continued)

*Primary Examiner* — Gregory J Toatley
*Assistant Examiner* — Dominic J Bologna
(74) *Attorney, Agent, or Firm* — Thomas C. Meyers; Brown Rudnick LLP

(57) ABSTRACT

The disclosed automatic calibration systems and methods provide a repeatable way to detect internal catheter reflections and to shift the internal catheter reflections to calibrate an image.

11 Claims, 23 Drawing Sheets

U.S. PATENT DOCUMENTS

| | | | |
|---|---|---|---|
| 7,463,362 B2 | 12/2008 | Lasker et al. | |
| 7,633,627 B2 | 12/2009 | Choma et al. | |
| 7,728,986 B2 | 6/2010 | Lasker et al. | |
| 7,936,462 B2 | 5/2011 | Jiang et al. | |
| 8,049,900 B2 | 11/2011 | Kemp et al. | |
| 2003/0220749 A1 | 11/2003 | Chen et al. | |
| 2005/0078317 A1 | 4/2005 | Law et al. | |
| 2005/0171438 A1 | 8/2005 | Chen et al. | |
| 2006/0039004 A1* | 2/2006 | de Boer et al. | 356/479 |
| 2006/0055936 A1 | 3/2006 | Yun et al. | |
| 2006/0187537 A1 | 8/2006 | Huber et al. | |
| 2006/0244973 A1 | 11/2006 | Yun et al. | |
| 2006/0264743 A1* | 11/2006 | Kleen et al. | 600/425 |
| 2007/0015969 A1 | 1/2007 | Feldman et al. | |
| 2007/0038121 A1 | 2/2007 | Feldman et al. | |
| 2007/0142707 A1* | 6/2007 | Wiklof et al. | 600/118 |
| 2007/0161893 A1 | 7/2007 | Milner et al. | |
| 2007/0260138 A1 | 11/2007 | Feldman et al. | |
| 2008/0095714 A1 | 4/2008 | Castella et al. | |
| 2008/0097194 A1 | 4/2008 | Milner | |
| 2008/0154128 A1 | 6/2008 | Milner | |
| 2008/0291463 A1 | 11/2008 | Milner et al. | |
| 2009/0174886 A1 | 7/2009 | Inoue | |
| 2009/0174931 A1 | 7/2009 | Huber et al. | |
| 2009/0284749 A1 | 11/2009 | Johnson et al. | |
| 2009/0290167 A1 | 11/2009 | Flanders et al. | |
| 2010/0128348 A1 | 5/2010 | Taverner | |
| 2010/0220334 A1 | 9/2010 | Condit et al. | |
| 2012/0013914 A1 | 1/2012 | Kemp et al. | |

FOREIGN PATENT DOCUMENTS

| | | |
|---|---|---|
| WO | 2004096049 A2 | 11/2004 |
| WO | 2006068875 A2 | 6/2006 |

OTHER PUBLICATIONS

Alazartech, "Specifications for ATS660 125 MS/s 16-bit PCI Digitizer", Version 1.1A, www.alazartech.com.

MA Choma, et al., "Sensitivity Advantage of Swept Source and Fourier Domain Optical Coherence Tomography", Optics Express, vol. 11, No. 18, pp. 2183-2189, (2003).

Gage Applied Technologies, "Specifications for CompuGen 4300/4302 High-Speed Arbitrary Waveform Generator Card", (May 29, 2006), www.gage-applied.com.

Gage Applied Technologies, "Specifications for CompuScope 1610 Ultra-Fast Waveform Digitizer Card for PCI Bus", (Mar. 31, 2006), www.gage-applied.com.

Eigenwillig et al., "K-Space Linear Fourier Domain Mode Locked Laser and Applications for Optical Coherence Tomography", Optics Express, vol. 16, No. 12, pp. 8916-8937, (2008).

Herget et al., "Infrared Spectrum of Hydrogen Fluoride: Line Positions and Line Shapes. Part II. Treatment of Data and Results", Journal of the Optical Society of America, vol. 52, pp. 1113-1117, (1962).

Huber et al., "Amplified, Frequency Swept Lasers for Frequency Domain Reflectometry and OCT Imaging: Design and Scaling Principles", Optics Express, vol. 13, No. 9, pp. 3513-3528, (2005).

Huber et al., "Fourier Domain Mode Locking (FDML): A New Laser Operating Regime and Applications for Optical Coherence Tomography", Optics Express, vol. 14, No. 8, pp. 3225-3237, (2006).

SMRM Nezam, "High Speed Polygon-Scanner-Based Wavelength-Swept Laser Source in the Telescope-Less Configurations with Application in Optical Coherence Tomography", Optics Letters, vol. 33, No. 15, pp. 1741-1743, (2008). Abstract Only.

Oldenburg et al., "Fast-Fourier-Domain Delay Line for In Vivo Optical Coherence Tomography with a Polygonal Scanner", Applied Optics, vol. 42, No. 22, pp. 4606-4611, (2003).

Sarunic et al., "Instantaneous Complex Conjugate Resolved Spectral Domain and Swept-Source OCT Using 3x3 Fiber Couplers", Optics Express, vol. 13, No. 3, pp. 957-967, (2005).

Vakoc et al., "Phase-Resolved Optical Frequency Domain Imaging:", Optics Express, vol. 13, No. 14, pp. 5483-5493, (2005).

Wavelength References, "Specifications for OEM Calibrators: Hydrogen Fluoride Gas Cell HF", www.wavelengthreferences.com.

Written Opinion for International (PCT) Patent Application No. PCT/US2008/070010, mailed Oct. 8, 2008.

* cited by examiner

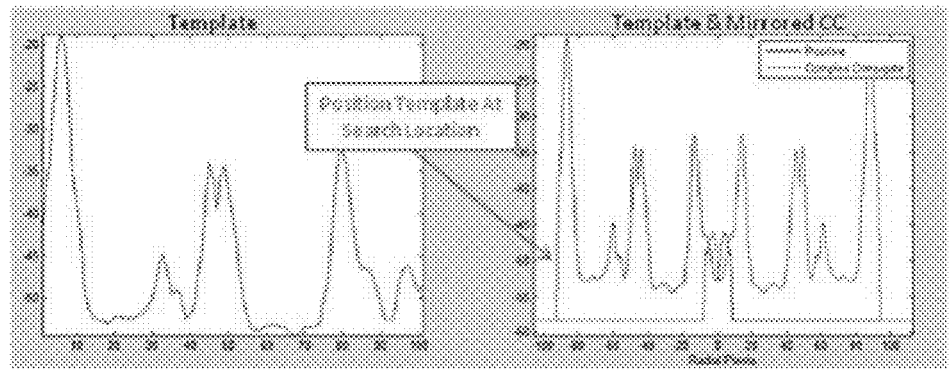
FIG. 18A  FIG. 18B
FIG. 18C  FIG. 18D
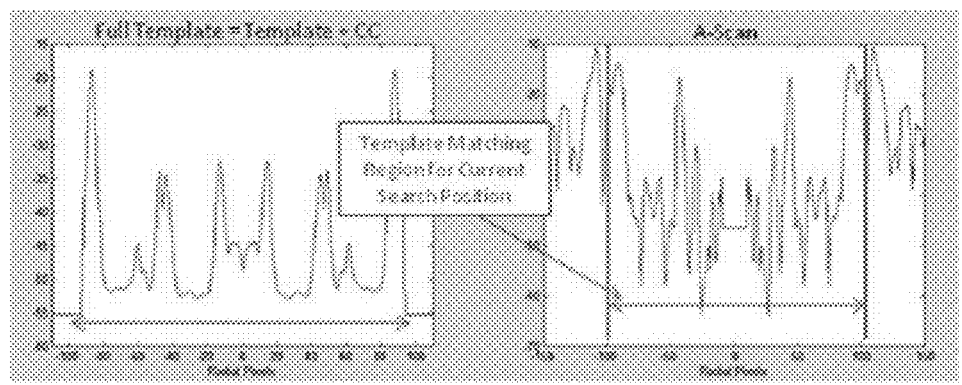
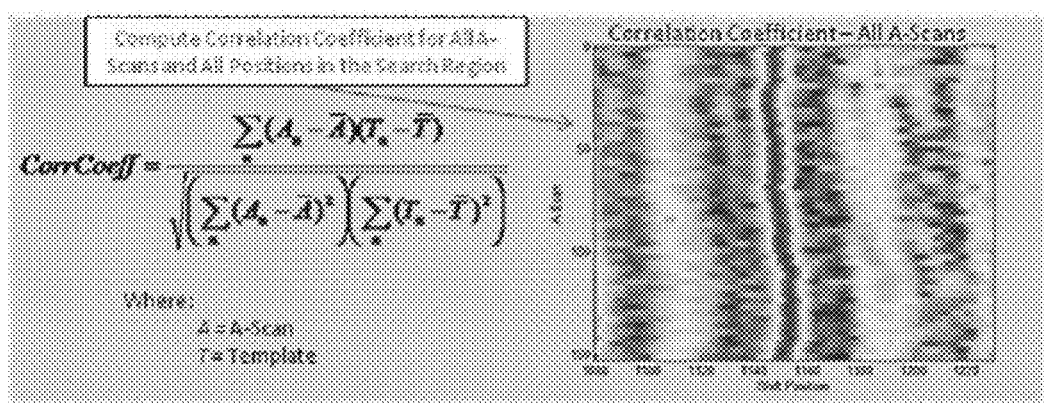
FIG. 19

AUTOMATIC CALIBRATION SYSTEMS AND METHODS OF USE

CROSS-REFERENCE TO RELATED APPLICATIONS

This is a continuation-in-part of U.S. patent application Ser. No. 13/243,399, which was filed Sep. 23, 2011, which is a continuation of Ser. No. 12/172,980 (now U.S. Pat. No. 8,049,900), which was filed Jul. 14, 2008 and which claims priority to U.S. Provisional Patent Application Ser. No. 60/949,467 filed Jul. 12, 2007, and the entirety of each of which is incorporated herein by reference.

FIELD OF THE INVENTION

The invention generally relates to calibration systems and methods of use, and more particularly to calibration systems for optical imaging systems.

BACKGROUND

Accurate Optical Coherence Tomography (OCT) measurements or dimensional analysis require the displayed tomographic image to correctly represent physical space (i.e. conversion from image pixels to physical mm). This requirement is complicated by factors such as varying object refractive indexes (catheter optics, sheath, lumen, tissue) and the arbitrary location (in z) of relevant image features due to mismatch in the interferometer's sample and reference paths.

Most current methods require the user to manually calibrate the image by adjusting the Z-Offset position (reference arm path length) until the outer diameter of the catheter sheath aligns with fixed tick marks on the screen. This method can be time consuming and lends itself to operator error. Additionally, once the catheter is shifted from the original calibrated position, the calibration can be thrown off due to time-varying mechanical strain (e.g. pullback motion or manipulation of PIM cable) or thermal changes (room temp vs. body temp).

SUMMARY OF THE INVENTION

The invention addresses the above-identified problems and relates to automatic calibration. A catheter can be calibrated, according to the invention, by taking an image in a catheter and utilizing a template to identify the position of the catheter reflection lines. Another way to calibrate a catheter is to image a catheter pullback, align the image data to ensure any shifts to the reflection positions during image acquisition are corrected, and track the reflection positions through each image frame. Yet another way to calibrate a catheter is take an image of a catheter, track the reflection lines of the catheter, not detect the reflection lines in an image, and reacquire the lost track image with a graph search step or a template matching step.

The foregoing and other features, advantages, and objects of the invention will become more apparent with reference to the disclosure that follows. The following description of exemplary embodiments, read in conjunction with the accompanying figures, is merely illustrative rather than limiting.

BRIEF DESCRIPTION OF THE DRAWINGS

The following brief descriptions are provided for a more complete understanding of the figures, but it should be understood that embodiments according to the invention are not necessarily limited to the precise arrangements and configurations shown.

FIGS. 18A-18D are graphs of the first step in the live tracking mode shifting the template to search the location and creating the "Full Template" with a mirrored signal.

FIG. 19 is a graph and equation for the second step in the live tracking mode for computing the correlation coefficient for the template and all A-scans, which is limited to template size.

DETAILED DESCRIPTION OF THE INVENTION

Figure 1:
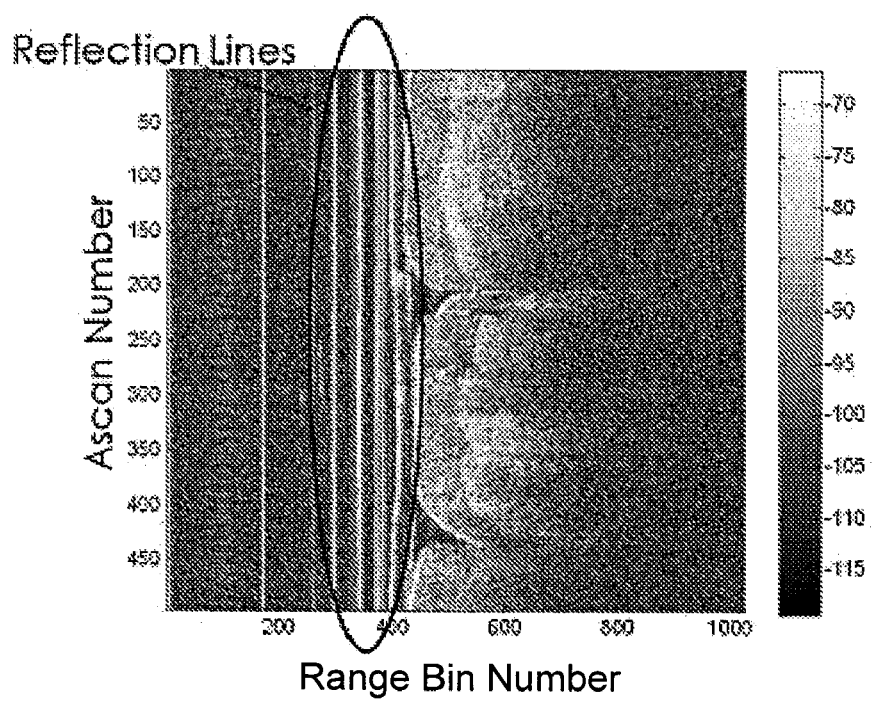
FIG. 1 is a graph showing the sample frame demonstrating catheter reflections used for calibration, in accordance with one embodiment.

In general, automatic calibration systems and methods according to the invention provide a repeatable way of detecting the internal catheter reflections and shifting the internal catheter reflections to calibrate an image. In one embodiment, the internal catheter reflections comprise reflections due to the end of the fiber optic cable, minor, lens, sheath, fluids, biological vessels, or any other objects that cause reflections and the like. The internal catheter reflections can be shifted mechanically and/or digitally. Generally, the automatic calibration comprises a first mode, a second mode, and a third mode. The calibration systems and methods update and maintain the calibration on a continuous frame-by-frame basis after an initial calibration.

An Optical Coherence Tomography (OCT) system may include a Fourier domain OCT ("FD-OCT"), sometimes known as Spectral Domain OCT ("SD-OCT"), or a Time-Domain OCT scanning ("TD-OCT"), where the optical path length of light in the reference arm of the interferometer is rapidly scanned over a distance corresponding to the imaging depth range. The OCT systems may be polarization-sensitive or phase-sensitive and adjusted accordingly. Alternatively, the imaging system may be any other optical imaging based system including, but not limited to spectroscopy, (including fluorescence, absorption, scattering, and Raman spectroscopies)

OCT Depth Calibration and Automated Range Adjustment

Circular and cylindrical OCT scanning devices, i.e. the rotation catheter scanning devices, sample physical space in an inherently polar coordinate system (e.g. radius and angle rather than length and width). Circular and cylindrical OCT scanning devices are applied to image physiological structures with cylindrical-like cross sections e.g., airways and blood vessel lumens). Digital representations of the images (i.e. arrays of pixels representing numeric values) are inherently rectangular. A method for detecting and using OCT image features, either intentionally or artifactually generated comprises automatically adjusting the depth range in polar ("radar-like") OCT images.

Polar OCT images are converted from their rectangular representation before displaying to the viewer on a video monitor or other physical display device. Additionally, if quantitative values (e.g. lumen diameters, lumen areas, circumferences, etc.) are to be measured on the polar image, then the transformation from rectangular-to-polar preserves relative distances between pixels in all dimensions (radial and angular). Generally, the OCT depth scan (y axis in rectangular coordinates) maps directly to radius and the OCT circumferential scan (x axis in rectangular coordinates) maps to some increment of 2*Pi radians (or 360°) polar angle.

For example: y=0 (the top row of the rectangular image) maps to radius=0 (the center of the polar image) and $y=y_{max}$ (the bottom row of the rectangular image) maps to radius=$y_{max}$ (the perimeter of the polar image). Likewise, x=0 (the left column in the rectangular image) maps to angle=0° and x=$x_{max}$/2 maps to approximately 180° and x=$x_{max}$ maps to an angle of approximately 359°.

For accurate quantitative dimensional measurement in polar images, pixels mapping to radius=0 represent the actual physical space at the center of the axis of rotation of the imaging probe, otherwise the polar image will be artificially warped (expanded or contracted) in the radial direction. However, in an arbitrary OCT image, the pixels at y=0 do not necessarily satisfy this requirement and must be shifted in the y-dimension until this is satisfied before mapping to a polar representation. Differential displacements (either controlled or uncontrolled) in the path length of the sample vs. reference arms of the interferometer will shift the pixels in the y-dimension.

Uncontrollable displacements can occur when using cylindrical or helical-scanning fiber-optic OCT catheters. For example, when the catheter is pushed or pulled longitudinally, the fiber-optic cable can be compressed or stretched and thus a path length displacement is incurred.

The method generally comprises automatically recognizing the uncontrolled displacement effect by searching for image features that are stationary but are not due to uncontrollable displacement, and calibrating successive OCT image data so that polar representations can be used for accurate dimensional measurements. In one embodiment, the method further comprises removing of image features in the image prior to display on a video monitor or other display device.

Image features used by the method are generated within the catheter itself (not within the imaged subject or surroundings) and appear somewhat stable in depth and consistent in intensity throughout the 360° rotation of the catheter. These image features include, but are not limited to, back reflections at interfaces between optical components (aka "ghost-lines" or "echo artifacts", these occur along the optical axis of rotating parts and thus appear as uniform circles in the polar image when no differential path length displacement occurs over the course of one catheter rotation), or reflections from the boundaries of or from within the stationary (non-rotating) catheter sheath (if it is circular in cross-sectional profile and also mechanically concentric with the rotating portion).

The embodiments disclosed herein include 3 methods for automatic calibration that utilize a plurality of back reflections to identify the required shift to achieve proper calibration. While there may be overlap between each of the 3 methods, each of the 3 methods are documented in a separate section for descriptive purposes only, and each of the 3 methods may be combined in alternative configuration, methods, parameters and the like. The first method includes an Automatic Calibration of the Z-offset, which is averaging and a general auto-calibration implementation. The second method includes an Automatic Calibration of Z-offset, which includes a Template Matching and a Graph Search method. The third method is an Automatic Calibration of Z-offset, which includes a Full Template Correlation.

Method 1: Automatic Calibration of Z-offset and Averaging. In one embodiment, steps in the automatic recognition and calibration method include: (1) Averaging the OCT image frame along the x- (i.e. angular) dimension to selectively enhance the feature(s) that are rotationally stable in the y-dimension (i.e. radius) vs. other image features generated by subject or surroundings. Efficacy of the averaging step is improved by selecting image feature(s) that have a high intensity relative to the surrounding pixels and if the subject/environment features (noise) do not have strong circumferential symmetry. In one embodiment, the method further comprises: (2) Finding image feature(s) using peak searching, correlation, thresholding, or other pattern recognition algorithms. Efficacy of the finding image features step is improved if the range over which uncontrolled path length displacements can occur is known a priori, thus limiting the required search space. In one embodiment, the method further comprises: (3) Comparing the y-value(s) of the image feature(s) found in step 2 to a pre-calibrated y-value that represents the actual physical location(s) of that image feature(s) relative to the rotational axis, or to the location of a known "conjugate image" or "aliased image" of that feature(s) when using spectral-domain OCT. In one embodiment, the method further comprises: (4) Calibrating by shifting the OCT image pixels in the y-dimension by the difference between searched image feature(s) and pre-calibrated image feature(s). Multiple features can be used to improve efficacy of the algorithm. After shifting the rectangular image in the y-dimension, mapping to polar image coordinates may take place. Radii measured to the center of the calibrated polar image represent actual radii measured to the rotational axis in physical space. Some image features due to the catheter are unwanted for effective and distraction-free display of the subject/environment features on a video monitor or other physical display device. For example, the catheter image features could overlap the subject/environment features.

In one embodiment, steps to remove (or make less noticeable) the image features include: cropping out the image feature(s) extent in the radial y-direction and in all columns/angles; calculating the average value of the pixels immediately inside and outside (above and below) of the cropped region for all columns/angles; and inserting this averaged row/circumference in the cropped location. The cropping operation can also remove subject/environment features and distorts the image in the radial dimension. This distortion makes measurement of accurate quantitative values on such images more complicated, because the measurement tool must then consider where pixels have and have not been cropped (or make the measurement on the un-cropped image).

In the calibration embodiment described above, the calibration method averages over a frame to identify a reflection, then adjusts the image digitally based on the feature location, and applies a constant shift for all A-scans within an image. An alternative method for an automatic calibration of the Z-offset uses internal catheter features that appear in the image to identify the required shift, which does not average the image intensities across a frame to find the image features, but uses a pattern of the reflections in the form of a template to identify the position of the reflections in an initial locking algorithm. "Template" generally refers to the catheter reflections pattern. This method applies a line-by-line shift to ensure that every A-scan is properly aligned for measurements in the playback mode algorithm. This method of Binary Template Matching and Graph Searching for Automatic Calibration of Z-offset is described in more detail below.

Method 2: Automatic Calibration of Z-offset and Template Matching and Graph Search. In one embodiment, the Automatic Calibration of Z-offset comprises a first mode of calibrating catheter reflections including an initial lock step. The initial lock comprises utilizing a template to identify the position of the catheter reflection lines unique to a particular catheter, as shown in FIG. 1. The template for each catheter is stored with the specific catheter. In one embodiment, the template is stored on a Radio Frequency Identification (RFID) chip, alternatively, the template may be stored on a computer chip, and the like. Alternatively, RFID or computer chip may be removable and then be used as a portable template or medical record. Alternatively, if the catheter is approved for reuse, the Patient Interface Module or PIM may down load specific information regarding the template for the particular catheter. This template information may be stored and tracked on the catheter monitor and limit the number of uses or hours of use to a predetermined amount also stored on the catheter. In one embodiment the RFID chip may be a Maxwell ME1 or ME2 RFID chip, mounted on the connector on the proximal end of the catheter for storing information and communicating with the interface device. In an alternative embodiment, the catheter may have a second RFID chip (not shown) mounted 180 degrees from the first RFID chip of the connector so catheter can be connected to interface device at more than one circumferential orientation. The RFID chip may have a memory of 128 bytes, alternatively 1K byte, alternatively 2K bytes alternatively 4K bytes to store catheter specific information, including for example catheter serial number, name, make or model, calibration coefficients, imaging element sensitivity, time gain control, post amp gain, number of permissible uses, geographic location of permissible use, boot mode, pulse width, or expiration date of the catheter.

Figure 2A:
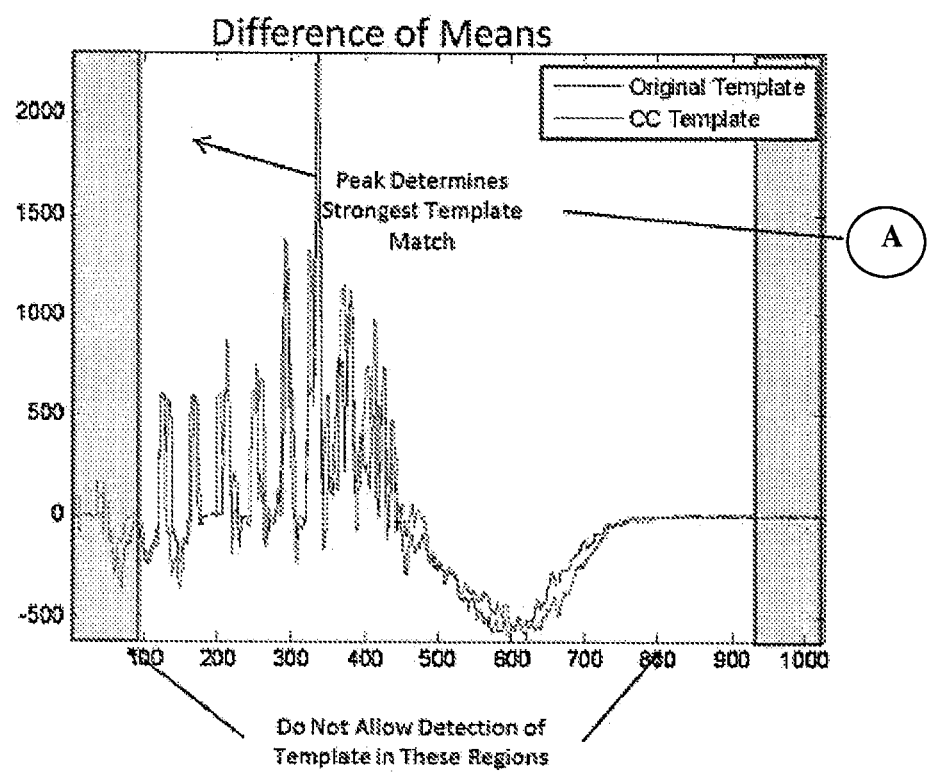
FIG. 2A is a graph of a template matching algorithm identifying a peak at bin 340, in accordance with one embodiment.
Figure 2B:
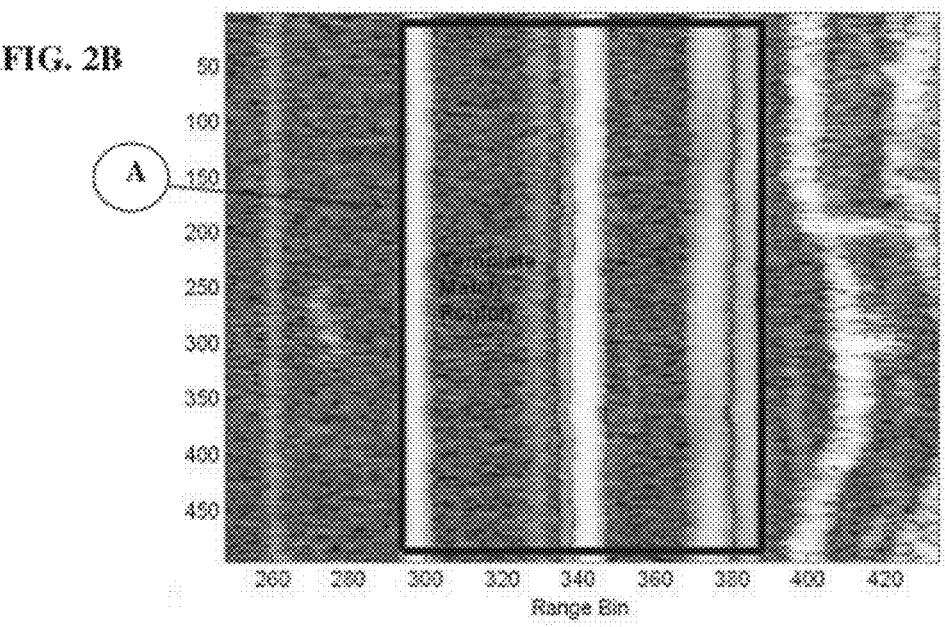
FIG. 2B is a graph of the zoomed in region A showing template match at bin 340, in accordance with one embodiment.

The template is convolved with a binary version of the gradient image and a peak is identified in a template matching step, as shown in FIG. 2A. The template matching step includes selecting a peak that corresponds to a strongest template match. In one embodiment, the peak is above a certain value to ensure that the strongest template match is identified. If no template match is identified, the Z-Offset position is adjusted and an image at the new position is evaluated with the template matching step or algorithm. Once the position of the catheter reflection lines are identified, the catheter reflection lines are shifted by adjusting the Z-Offset to move the reflections to their desired location and the image/catheter is now calibrated, as shown in FIG. 2B. In one embodiment, the adjusting Z-Offset comprises the mechanical shifting of the Variable Delay Line (VDL)). If the template matching algorithm is unable to identify a strong template match, the user is warned and given the option to retry auto-calibration or manually calibrate.

Figure 3:
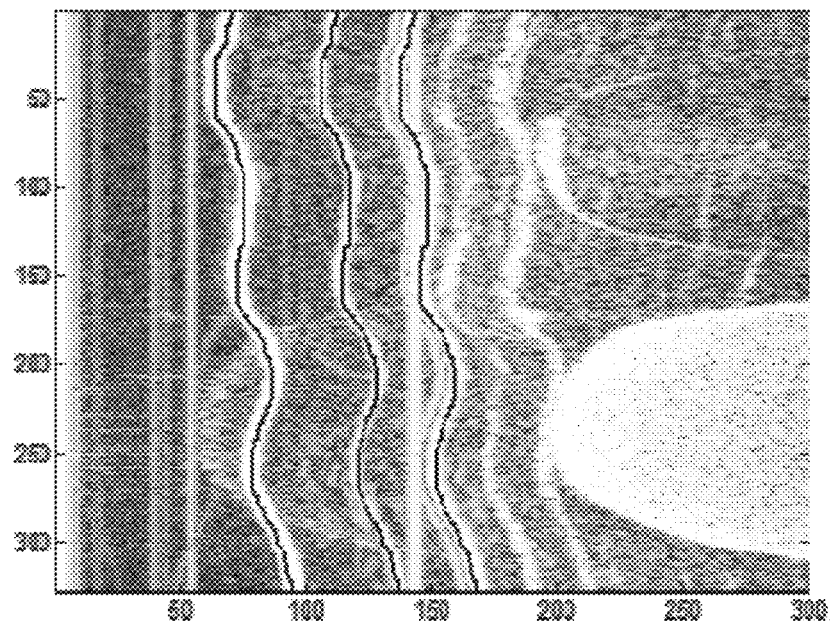
FIG. 3 is an enlarged image of reflection motion through one frame (motion due to tortuous pull back), in accordance with one embodiment.
Figure 4:
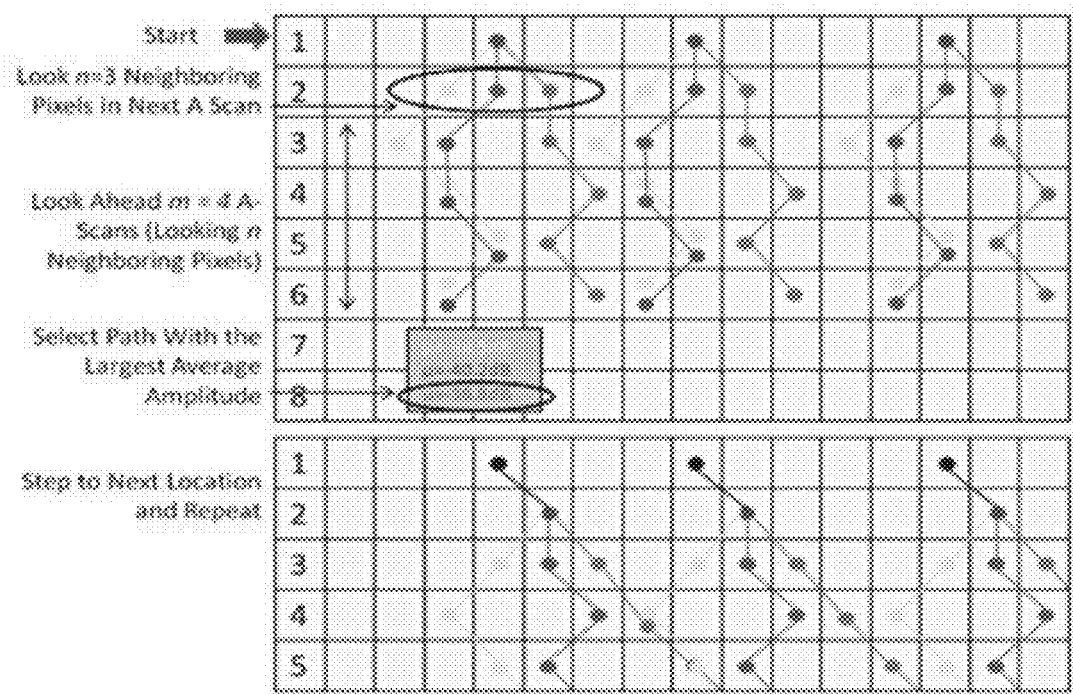
FIG. 4 is a graph search algorithm, in accordance with one embodiment.

In one embodiment of Method 2 for the Automatic Calibration of Z-offset for the Template Matching and Graph Search, the second mode of calibrating catheter reflections comprises playback tracking. Playback tracking generally includes aligning the image data after recording a catheter pullback to ensure any shifts to the reflection positions during acquisition are corrected to allow for proper analysis and/or measurements. Tracking the reflections through the recorded dataset is slightly more difficult due to the motion during pullbacks and the position of the reflections can vary significantly over a single frame. FIG. 3 demonstrates an example of significant shifting of the catheter reflections during a tortuous pullback. A graph searching step or algorithm is utilized to track the reflection through each frame. The graph search initial is identified by the template matching step or algorithm described above. Once an initial lock is acquired, the reflection lines are tracked through the image based on their amplitude and relative position. In one embodiment, the lines are tracked through the image based on their amplitude and relative position by maintaining a constant distance. The graph search step begins at the first A-scan and then looks at the neighboring pixels in the following A-scan to determine the direction for the next step. This process is then repeated for each A-scan. The algorithm also allows for "look ahead" which includes evaluating the next A-scan and looking ahead at the next "n" A-scans before determining the step direction. The black lines tracing the reflection in FIG. 3 demonstrate the results of the graph search algorithm. FIG. 4 provides a slightly more detailed explanation of the graph search algorithm. Once the lines have been traced through an entire frame they are digitally aligned and the frame is then properly calibrated for display and measurements.

Figure 5:
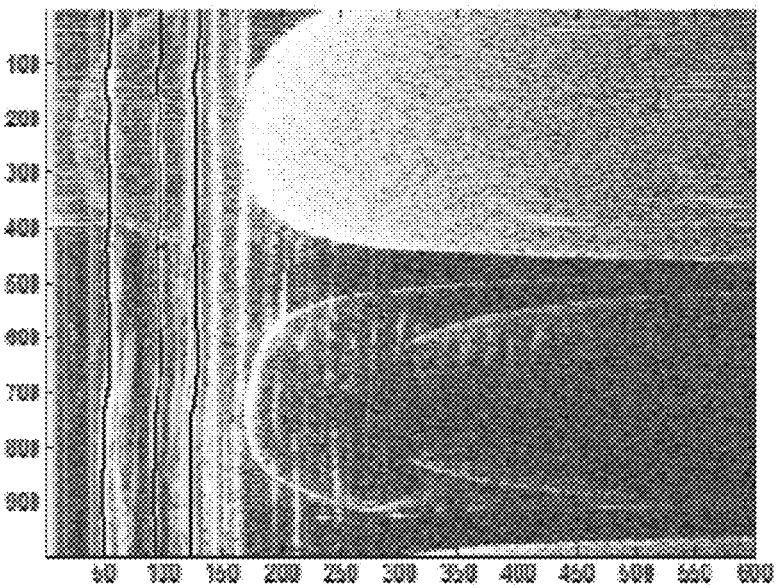
FIG. 5 is an image frame of a catheter pullback sequence and the track maintained through image frame, in accordance with one embodiment.
Figure 6:
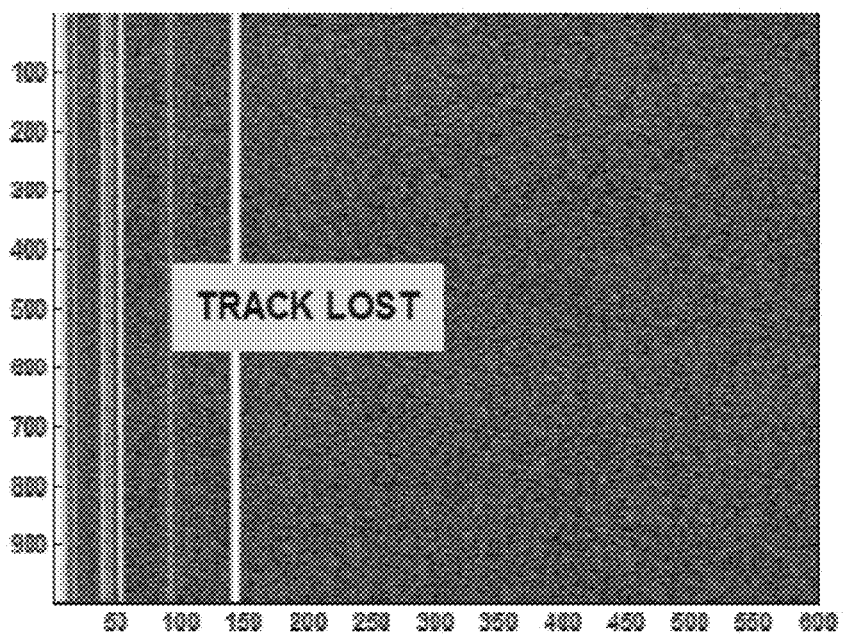
FIG. 6 is an image frame 40 of a catheter pullback sequence and the catheter reflection lines not being present and the track is lost, in accordance with one embodiment.
Figure 7:
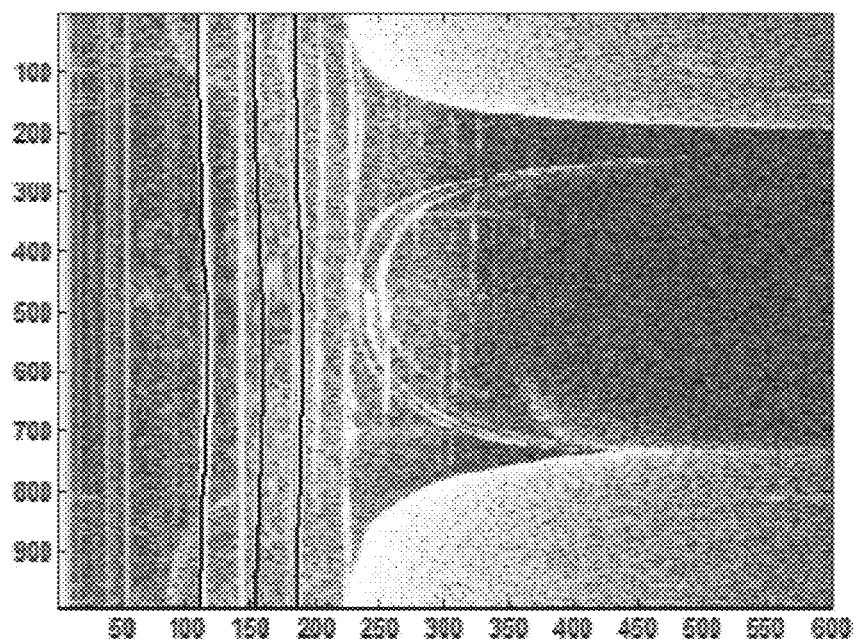
FIG. 7 is an image frame 50 of a catheter pullback sequence and the catheter reflections reappearing and the track reacquired for autocalibration, in accordance with one embodiment.

In one embodiment, the third mode of calibrating catheter reflections comprises a reacquiring lost track step. The reacquiring lost track step comprises reacquiring a track if the reflection lines are not detected in the previous image frames. As shown in FIGS. 5-7, the track of the reflections are lost during a tortuous pullback and then reacquired once the reflections reappear. To reacquire a lost track both the graph search step 220 and the template matching algorithms may be used. The graph search step expands the region of allowable solutions to search a wider number of bins for the reappearing reflections. A "guard band" is identified to limit the possible search region and prevents from locking on to the bright returns from the vessel wall. The template matching step may also be performed as described in the Initial Locking step. Once the track is reacquired, the algorithm transitions back to Playback Tracking mode to continue tracking the reflections through each subsequent frame.

Figure 8A:
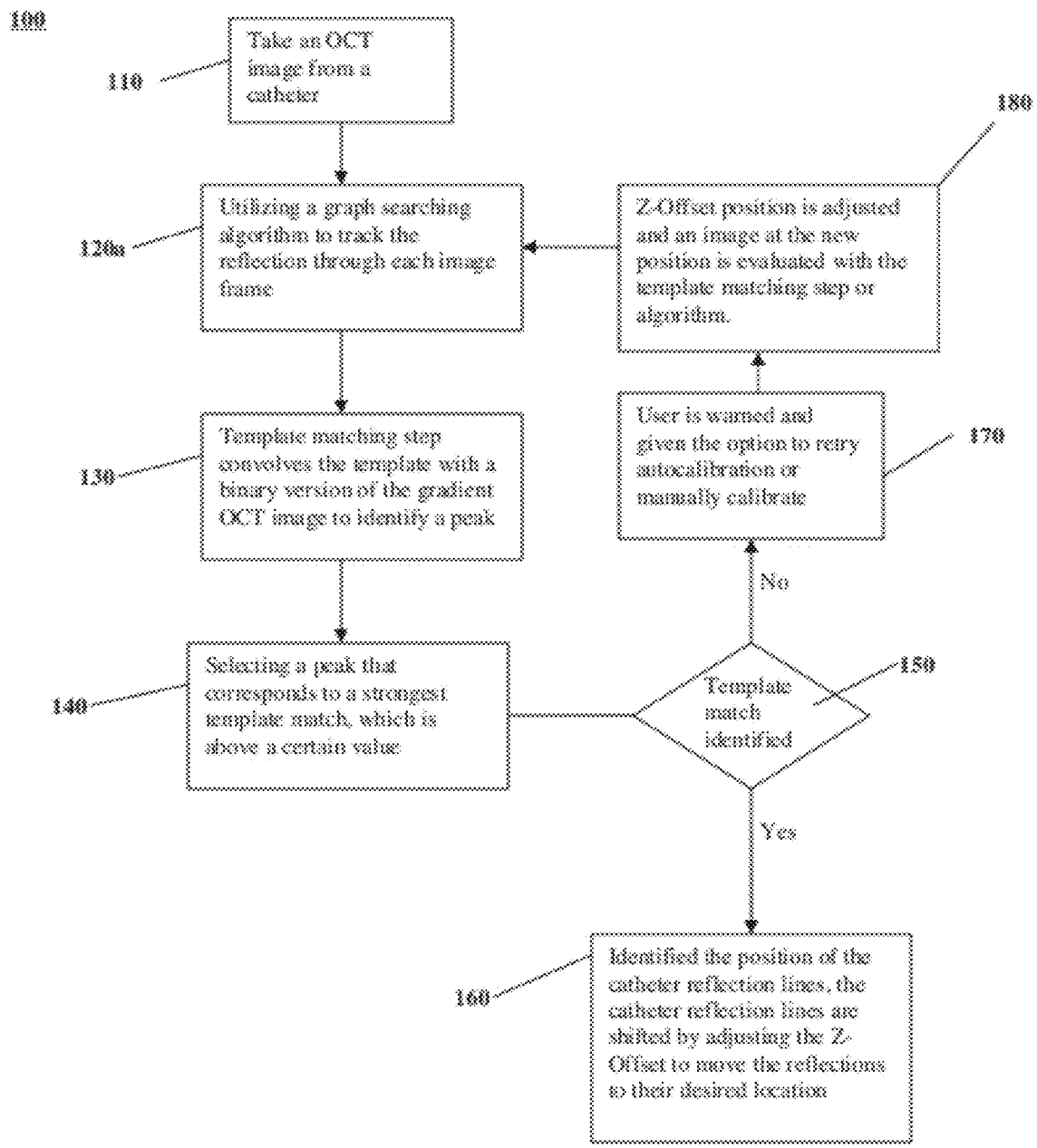
FIG. 8A is a flowchart displaying the first mode of the template matching step 100, in accordance with one embodiment.

With reference to FIG. 8A, an illustrated method of the first mode and the initial lock step 100 is shown. The process begins at step 110 by taking an OCT image in a catheter. Then, step 120a utilizes a template to identify the position of the catheter reflection lines unique to a particular catheter from a module or other software device, as shown in FIG. 2B. The template for each catheter is stored or operably accessible with the specific catheter. In one embodiment, the template is stored on a Radio Frequency Identification (RFID) chip or transponder or tag; alternatively, the template may be stored on a computer chip, cache, flash drive, and any other storage medium. The template matching step or algorithm 130 convolves the template with a binary version of the gradient OCT image and a peak is identified, as shown in FIG. 2A. The template matching step includes step 140 for selecting a peak that corresponds to a strongest template match. In one embodiment, the peak is above a certain value to ensure that the strongest template match is identified. If no template match is identified in decision 150, the method proceeds to step 170 where the Z-Offset position is adjusted and an image at the new position is evaluated with the template matching step or algorithm 130. If the template matching algorithm is unable to identify a strong match, the user is warned and given the option to retry auto-calibration or manually calibrate. If a template match is identified in decision 150, the position of the catheter reflection lines are identified, the catheter reflection lines are shifted by adjusting the Z-Offset to move the reflections to their desired location, and the image/catheter is now calibrated, as shown in FIG. 2B. In one embodiment, the adjusting Z-Offset comprises the mechanical shifting of the Variable Delay Line (VDL).

Figure 8B:
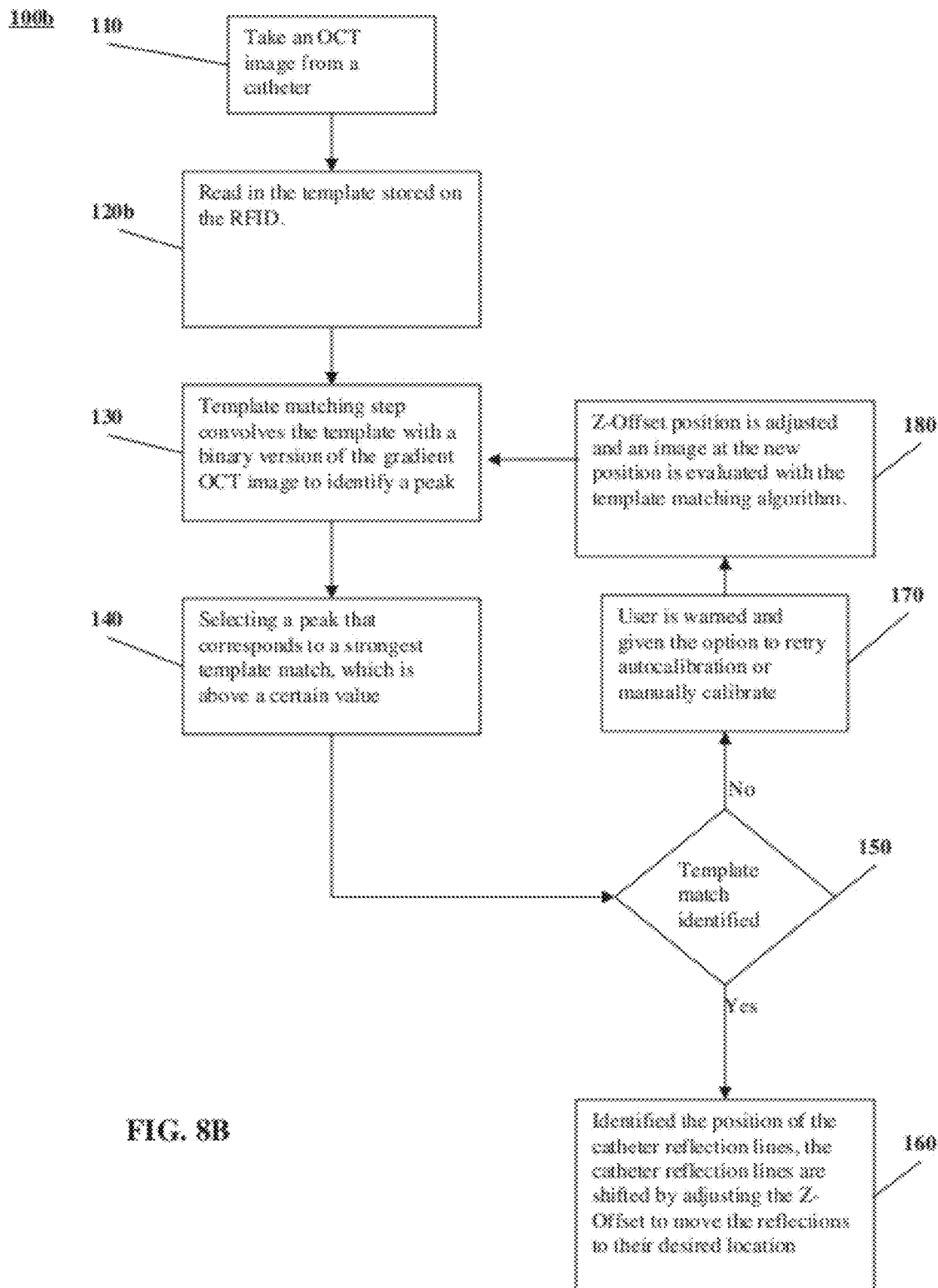
FIG. 8B is a flowchart displaying the first mode of the template matching step 100, in accordance with an alternative embodiment.

With reference to FIG. 8B, an alternative method of the first mode and the initial lock step 100b is shown. The process 100b begins similar as process 100a at step 110 by taking an OCT image in a catheter. Then, step 120b utilizes a template to identify the position of the catheter reflection lines unique to a particular catheter from a module or other software device, as shown in FIG. 2B. The template for each catheter is stored or operably accessible with the specific catheter. In one embodiment, the template is stored on a Radio Frequency Identification (RFID) chip or transponder or tag; alternatively, the template may be stored on a computer chip, cache, flash drive, and any other storage medium. The template matching step 130 convolves the template with a binary version of the gradient OCT image and a peak is identified, as shown in FIG. 2A. The template matching step includes step 140 for selecting a peak that corresponds to a strongest template match. In one embodiment, the peak is above a certain value to ensure that the strongest template match is identified. If no template match is identified in decision 150, the method proceeds to step 180 where the Z-Offset position is adjusted and an image at the new position is evaluated with the template matching step 130. If the template matching algorithm is unable to identify a strong template match, the user is warned and given the option to retry auto-calibration or manually calibrate. If a template match is identified in decision 150, the position of the catheter reflection lines are identified, catheter reflection lines are shifted by adjusting the Z-Offset to move the reflections to their desired location, and the image/catheter is now calibrated, as shown in FIG. 2B.

Figure 9:
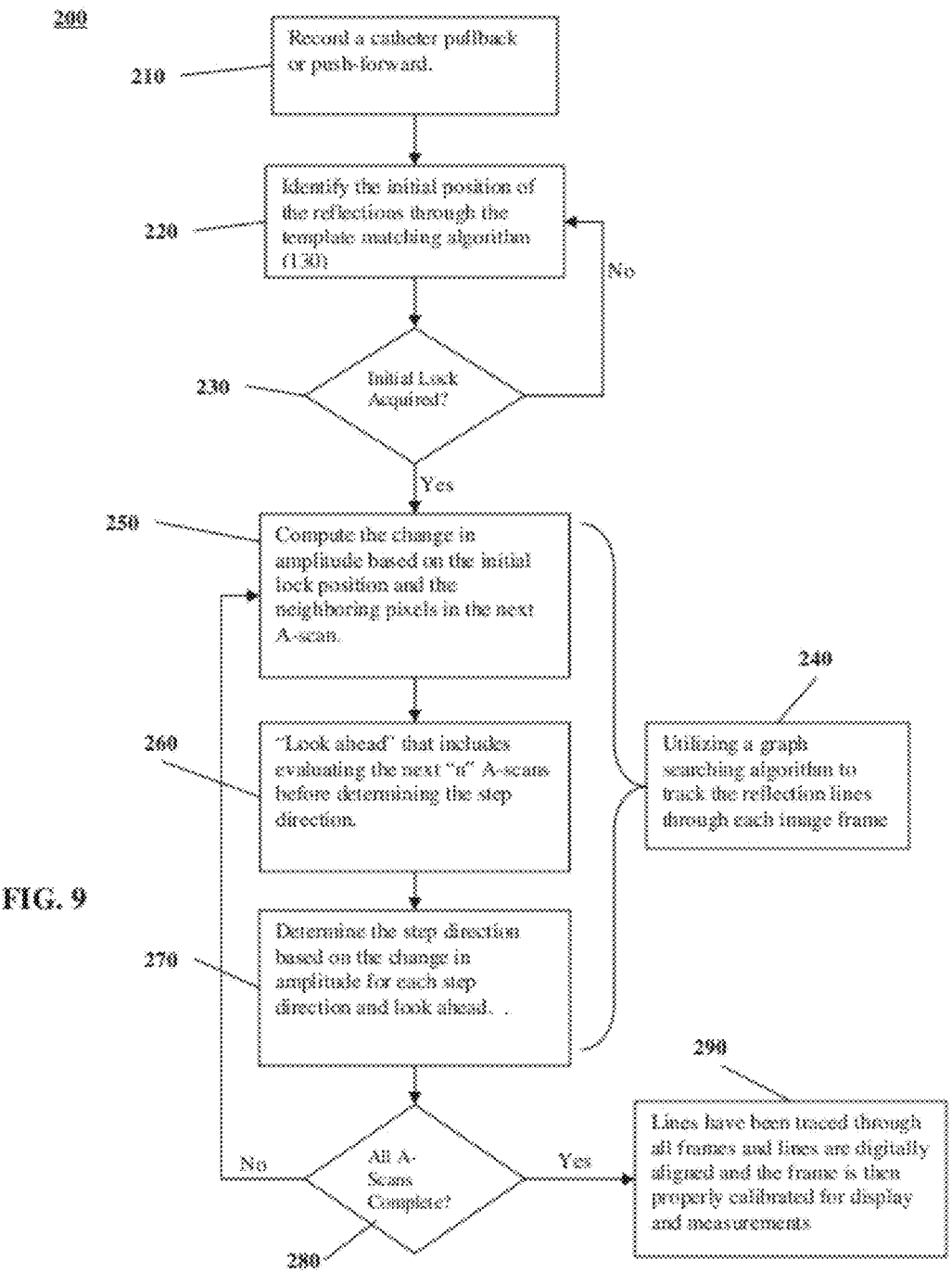
FIG. 9 is a flowchart displaying the second mode of the playback tracking step 200, in accordance with one embodiment.

With reference to FIG. 9, an illustrated method of the second mode and the playback tracking 200 is shown. The playback tracking method 200 begins with step 210 of recording a catheter pullback or push-forward. The objective of the playback mode tracking is to digitally align the image data to ensure any shifts to the reflection positions during image acquisition are corrected to allow for proper analysis and/or measurements. Tracking the reflections through the recorded dataset is slightly more difficult due to the motion during pullbacks and the position of the reflections can vary significantly over a single frame. FIG. 3 demonstrates an example of significant shifting of the catheter reflections during a tortuous pullback. The playback tracking method, 200, utilizes a graph searching algorithm to track the reflection through each image frame. Prior to beginning the graph search algorithm in step 220 the initial position of the reflections are identified using the template matching algorithm described 130 above. Once an initial lock 230 is acquired, step 240 tracks the reflection lines through the image based on their amplitude and relative position. In one embodiment, the lines are tracked through the image based on their amplitude and relative position by maintaining a constant distance. Step 250 begins with the first A-scan, then looks at the neighboring pixels in the following A-scan to determine the direction for the next step, and repeated for each A-scan. Step 260 allows for "look ahead" that includes evaluating the next A-scan and looking ahead at the next "n" A-scans before determining the step direction. Step 270 uses the information from steps 250 and 260 to determine the direction of the reflections in the current A-Scan. In 280 the algorithm increments to the next A-Scan and repeats the same processing until all A-Scans in the playback have been evaluated. The black lines tracing the reflection in FIG. 3 demonstrate the results of the graph search algorithm. FIG. 4 provides a slightly more detailed explanation of the graph search algorithm. Step 290 traces the reflection lines through an entire frame they are digitally aligned and the frame is then properly calibrated for display and measurements.

Figure 10:
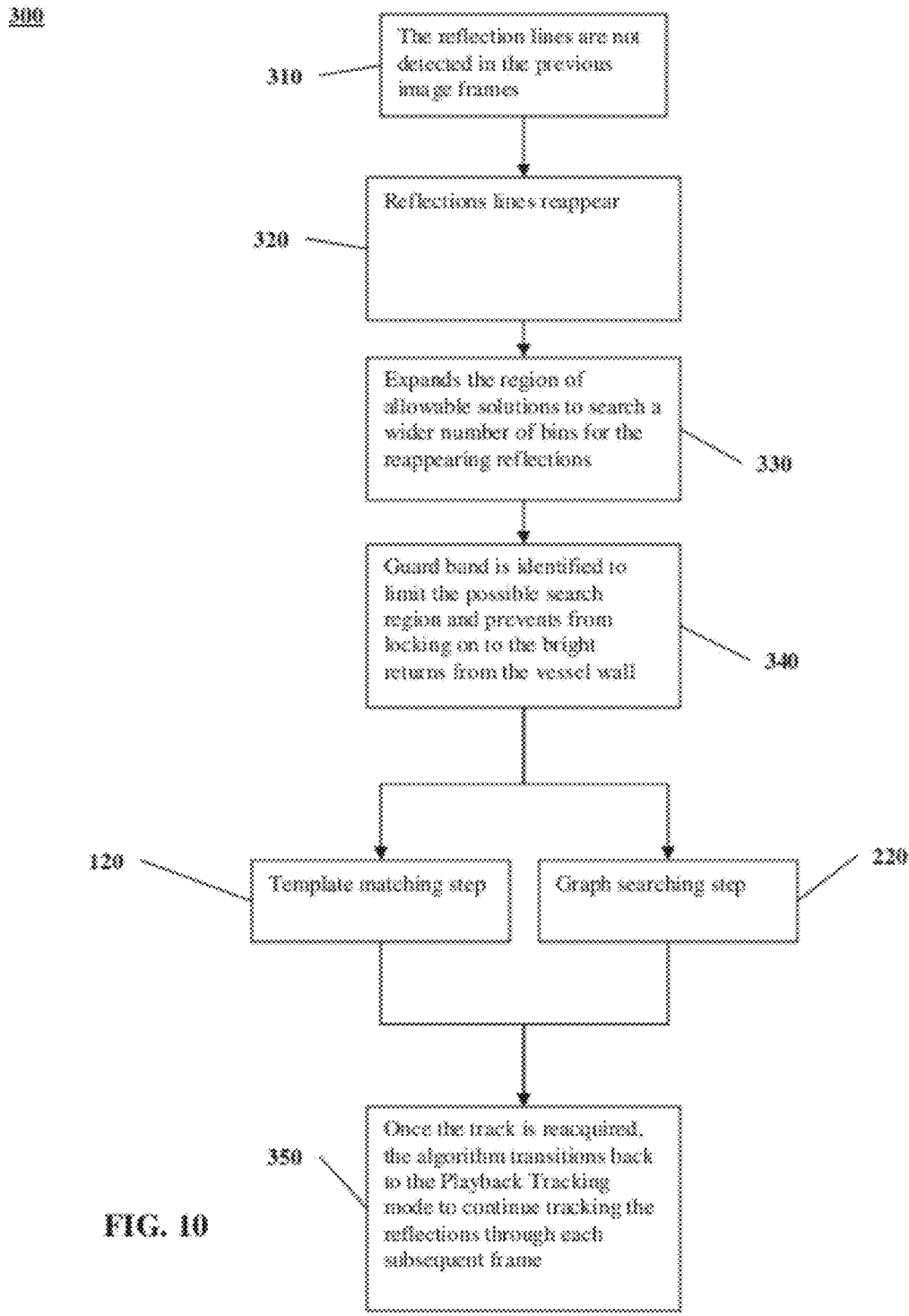
FIG. 10 is a flowchart displaying the third mode of the reacquiring lost track step 300, in accordance with one embodiment.

With reference to FIG. 10, an illustrated method of the third mode and the reacquiring lost track method 300 are shown. The reacquiring lost track method 300 begins at step 310 if the reflection lines are not detected in the previous image frames. In one embodiment, the reflection lines may be lost during a tortuous pullback of the catheter. Once the reflections reappear at step 320, the lost track may be reacquired with the graph search step 220 and the template matching algorithms 120, as indicated above. The graph search step 220 expands the region of allowable solutions to search a wider number of bins for the reappearing reflections in step 330. In step 340, the "guard band" is identified to limit the possible search region and then locking on to the bright returns from the vessel wall is prevented. The template matching step 120 may also be performed as described in the Initial Locking step above. In step 350, once the track is reacquired, the algorithm transitions back to the Playback Tracking mode to continue tracking the reflections through each subsequent frame.

Figure 11:
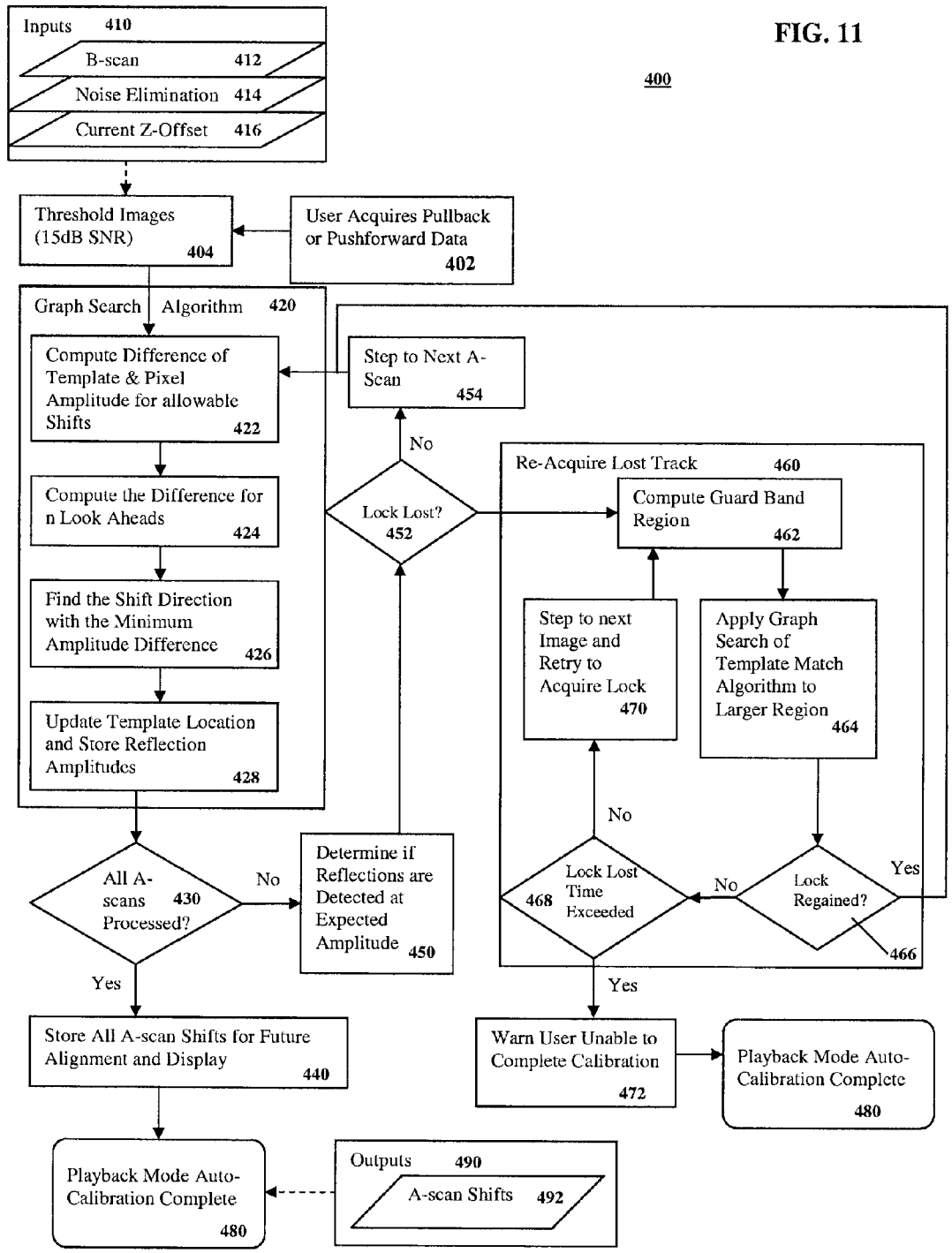
FIG. 11 is a flowchart displaying the auto-calibration in playback method 400, in accordance with one embodiment.

With reference to FIG. 11, an alternative embodiment of the auto-calibration in playback method 400 is shown. The method 400 generally comprises acquiring pullback or push-forward data 402 and obtaining a threshold image 404. A number of inputs 410 may be coupled to the threshold image, such as B-Scan data 412, noise estimates 414, or current Z-offset 416. Next, step 420 is the graph search algorithm 420, which includes computing the difference of template and pixel amplitude for allowable shifts 422, computing the difference for n-look aheads 424, finding the shift direction with the minimum amplitude difference 426, and updating the template location and storing the reflection amplitudes 428. Next, decision 430 determines if all A-scans have been processed. If so, the method proceeds to step 440 in storing all A-scan shifts for future alignment and display, and then playback method for autocalibration is complete 480. A further output 490 may include the data of the A-scan shift 492 for the playback method 400. If all the A-scans have not been processed at decision 430, then step 450 is determining if reflections are detected at an expected amplitude value. Decision 452 determines if the lock is lost. If the lock is not lost, the step 454 proceeds to step to the next A-scan and to the Graph Search algorithm 420 and step 422 of computing the difference of template and pixel amplitude values for allowable shifts. If the lock is lost, then the Re-Acquire the lost track step 460 is implemented. The Re-Acquire lost track step 460 begins with step 462 of computing the guard band region, then applying the graph search step of the template matching algorithm to the larger region in step 464, as described previously. Next, decision 466 determines if the lock has been regained. If the lock has been regained, then the Graph Search algorithm 420 is initiated and the step 422 of computing the difference of template and pixel amplitude values for allowable shifts. If the lock has not been regained, decision 468 determines if the lock lost time has been exceeded. If the lock lost time has been exceeded, the step 472 warns the user that calibration is unable to be completed, and the playback method of the auto-calibration is complete in step 480 to be reinstituted or adjusted by the user. If the lock lost time has not been exceeded, step 470 steps to the next image and retries to acquire the lock and proceeds to step 462 to compute the guard band region once again in the Re-Acquire track step 460.

Figure 12:
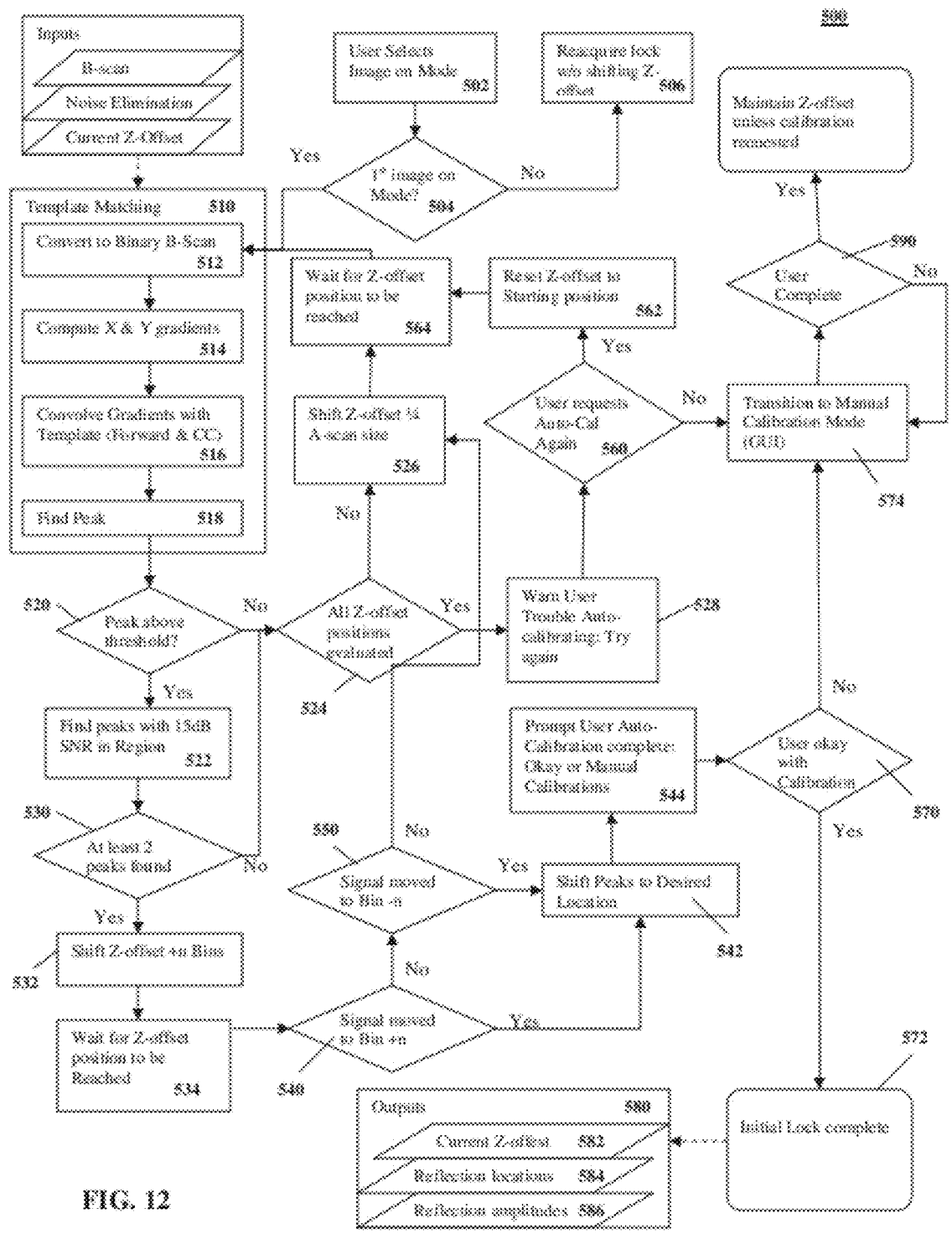
FIG. 12 is a flowchart displaying the auto-calibration initial lock method 500, in accordance with one embodiment.
Figure 13A:
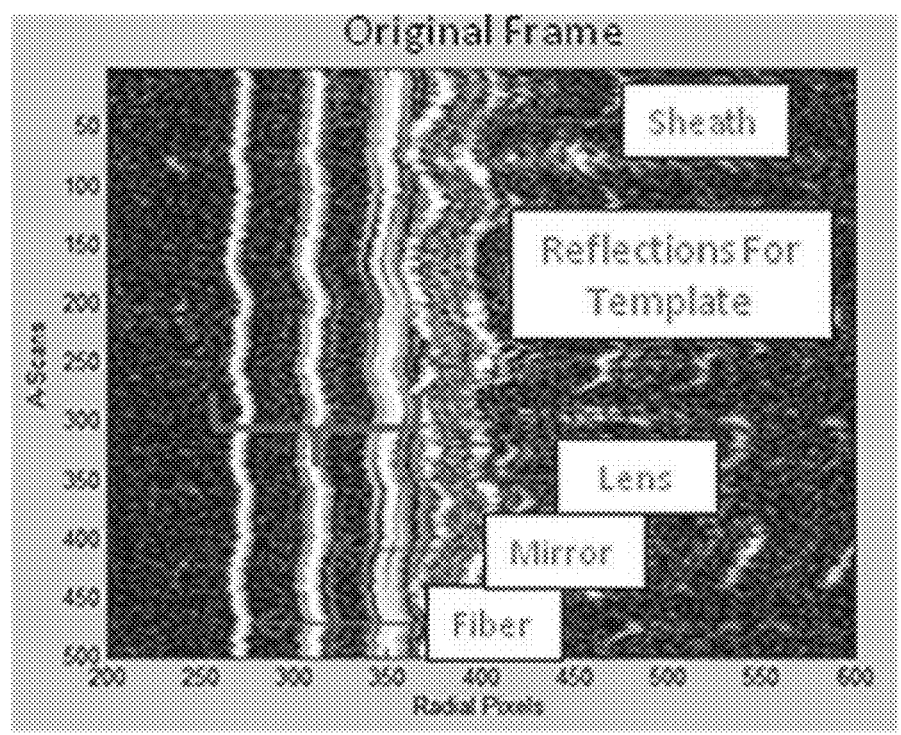
FIGS. 13A-13D are graphs of the first step in the initial lock mode of searching for a strong reflection using the mean amplitude or gradients and adjusting the Z-Offset until detected.
Figure 13B:
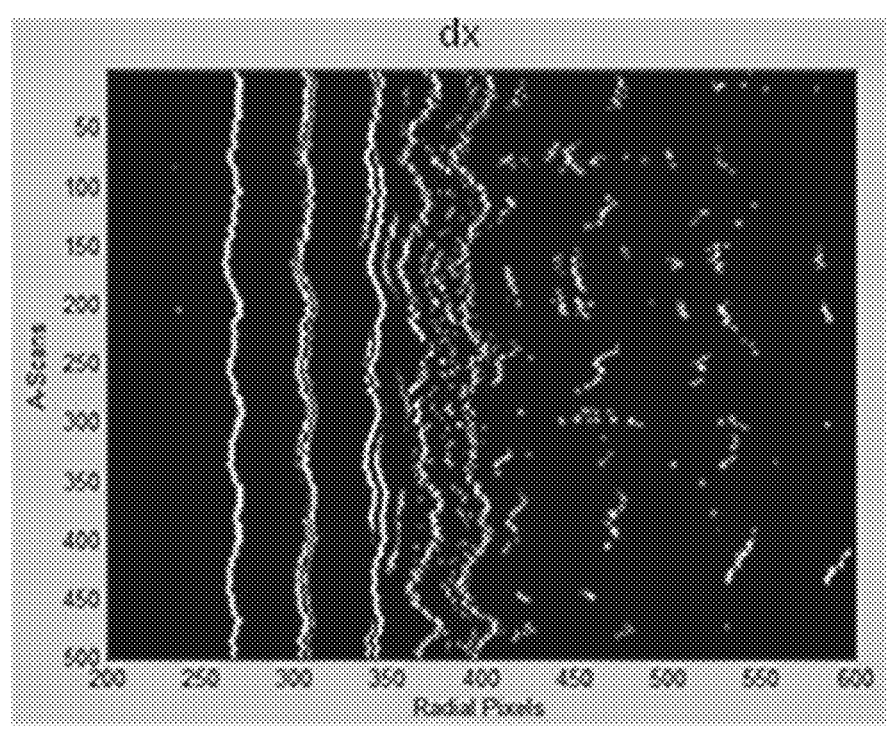
Figure 13C:
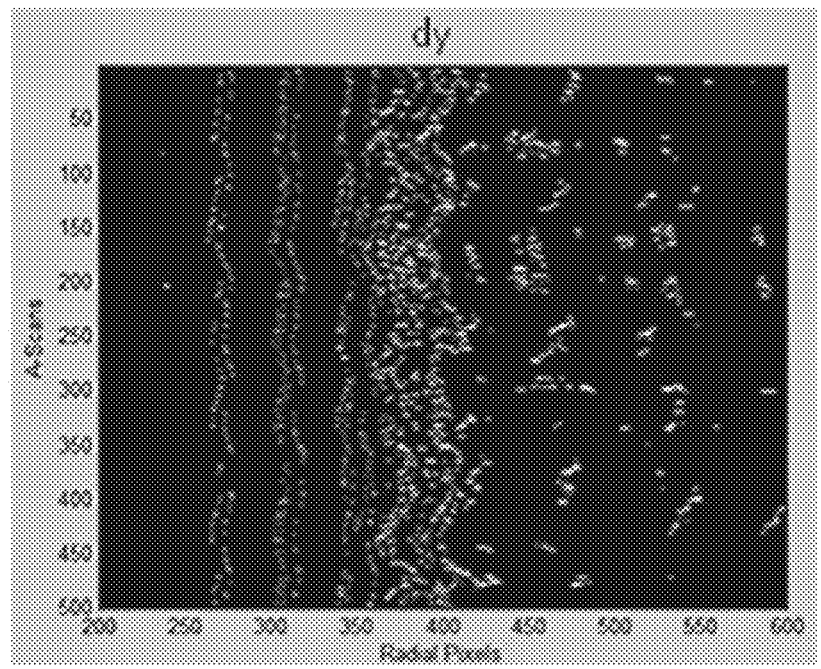
Figure 13D:
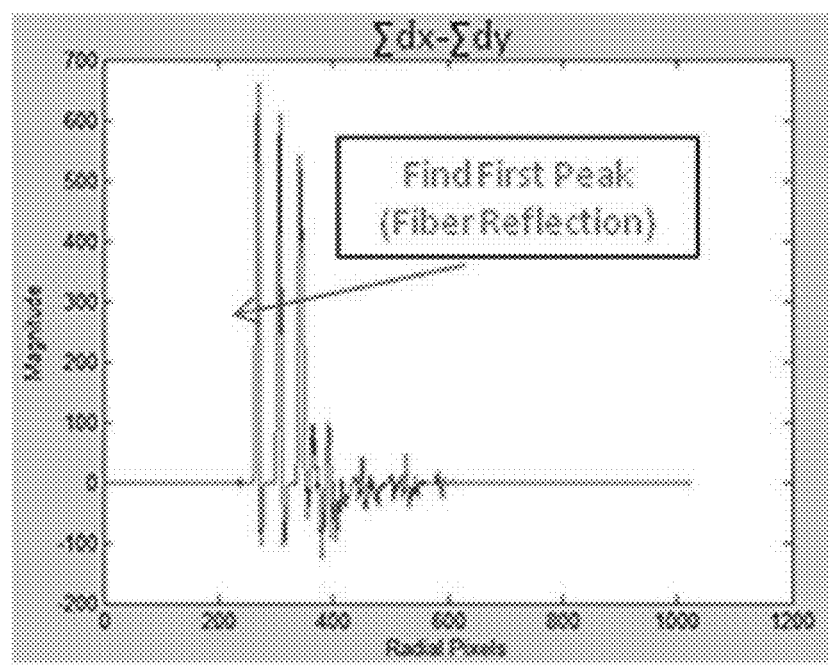

With reference to FIG. 12, an alternative embodiment of the auto-calibration initial lock method 500 is shown. The method 500 generally comprises selecting an image on mode and proceeds to decision 504 to determine whether the first image is on mode. If it is not the first instance of the image on mode for a catheter, step 506 proceeds in reacquiring the lock without shifting the Z-offset position. If it is the first instance of the image on mode, then the template matching step 510, as described above. The template matching step 501 starts with step 512 of converting the image to a binary B-scan, proceeds to step 514 of computing the X and Y gradients, proceeds to step 516 convolving the gradients with the template (Forward and CC), and finds the peak 518 at step 518. The template matching step 510 is finished and proceeds to decision 520 to determine if the peak threshold is obtained. If the peak threshold is obtained, then step 522 finds the peak with a signal-to-noise ratio threshold in the region. If the peak threshold is not obtained, then decision 524 determines if the all the Z-offset positions have been evaluated. Step 522 proceeds to decision 530 to determine if at least 2 peaks have been found. If at least two peaks have not been found, then decision 524 is initiated. If at least two peaks have been found, then step 532 shifts the Z-offset to +n Bins. Then step 534 waits for the Z-offset position to be reached and proceeds to decision 540. Decision 540 determines if the signal is moved to Bin +n. If the signal is moved to Bin +n, the step 542 shifts the peaks to the desired location. If the signal is not move to Bin +n, the Decision 550 determines if the signal is moved to Bin −n. If the signal is moved to Bin −n, then it proceeds to step 542. If the signal is not moved to Bin −n, then it proceeds to Decision step 526 to shift the Z-offset ¼ of the A-scan size. Decision 524 also shifts to step 526 if all the Z-offset positions have not been evaluated. If all the Z-offset position have been evaluated, then step 528 warns the user that there is trouble in the auto-calibration and to try initiation of the method 500 again. Then step 528 proceeds to Decision 560 to determine if the user is requesting the auto-calibration method again. If the user is requesting the auto-calibration method again, then step 562 resets the Z-offset to the starting position. Step 562 then proceeds to step 564 to wait for the Z-offset position to be reached, which then proceeds to the template matching step 510 and step 512 of converting the image to a binary B-scan.

Step 542 proceeds to step 544 to prompt the user that auto-calibration is complete for entry of manual calibrations or accepting the auto-calibration. Step 544 then proceeds to decision 570, which determines if the user is okay with the calibration. If the user accepts the calibration, then the initial lock method is complete in step 572. The outputs 580 for the initial lock include the current Z-offset 532, the reflection locations 584, or the reflection amplitudes 586. If the user does not accept the calibration, then step 574 transitions to manual calibration mode through a Graphical User Interface (GUI). Then decision 590 allows the user to complete the calibration. If the user completes the calibration, then step 592 maintains the Z-offset unless calibration is further requested. If the user does not complete the calibration, the step 574 transitions to manual calibration mode for additional attempts by the user.

Automatic Calibration of Z-offset Method 3: Auto-Template Generation and Full Correlation. Alternatively, the template may not be stored on a memory chip or the RFID, as in the previous Method 2, and the template may be automatically generated during an initial lock mode process, as described below for Method 3. The previous method utilized a binary template for template matching, while Method 3 generates a template with amplitude information and the complex conjugate signal information. Utilizing amplitude information and generating the minor signal increases the likelihood of locking on to the correct reflection lines. Additionally, Method 3 step or algorithm performs Auto-Calibration during initial lock and playback mode, and Method 3 also maintains calibration during a live mode (when the catheter is imaging but is not recording data).

In one embodiment for the first mode is the initial lock, which utilizes the internal catheter reflections (fiber, minor and lens) to identify the required VDL shift to reach the calibration position, as described in previous methods. The initial lock Z-Offset calibration is the step in which the reflection pattern or the template is determined. The template identified in the initial Z-offset calibration is utilized in each subsequent calibration mode to track the shift of the reflections and apply the analog and digital shifts, as required or implemented. The template region is identified using gradient and amplitude information. Once the template is identified and stored for later use, the VDL shift is applied and the catheter is ready for calibration during live and playback mode. Acceptable error in this position will be determined by the ability of the next mode (maintenance of Z-offset during live imaging) to lock onto the reference pattern of catheter reflection lines in the OCT image.

FIGS. 13-16 provide an overview of the alternative steps for the initial Z-Offset calibration. FIGS. 13A-13D are graphs of the first step in the initial lock mode of searching for a strong reflection using the mean amplitude or gradients and adjusting the Z-Offset until detected. FIG. 13A shows that there are reflections present for the fiber, mirror, lens, sheath, and reflections for the template. The algorithm utilizes X and Y gradients of the image to determine if reflections are present. FIG. 13B is the change of the X gradient and FIG. 13C is the change of the Y gradient. If no reflections are found, the VDL is shifted to the next possible Z-offset location. Once strong reflections are identified, a slight positive VDL shift is applied to verify the orientation of reflections. If the reflections shift towards the center of the image, then the reflections are oriented properly for calibration. If the reflections shift outward, the image is the complex conjugate signal and a large negative VDL shift is applied to unwrap the image. After the image is determined to be properly oriented, the reflections are shifted to the center of the window to ensure the full template region is visible. If at any point during each of the shifting steps the reflection lines are no longer detected, the algorithm applies a new Z-offset and starts over looking for strong returns. FIG. 17 provides a more detailed version of the algorithm and user interaction.

Figure 14A:
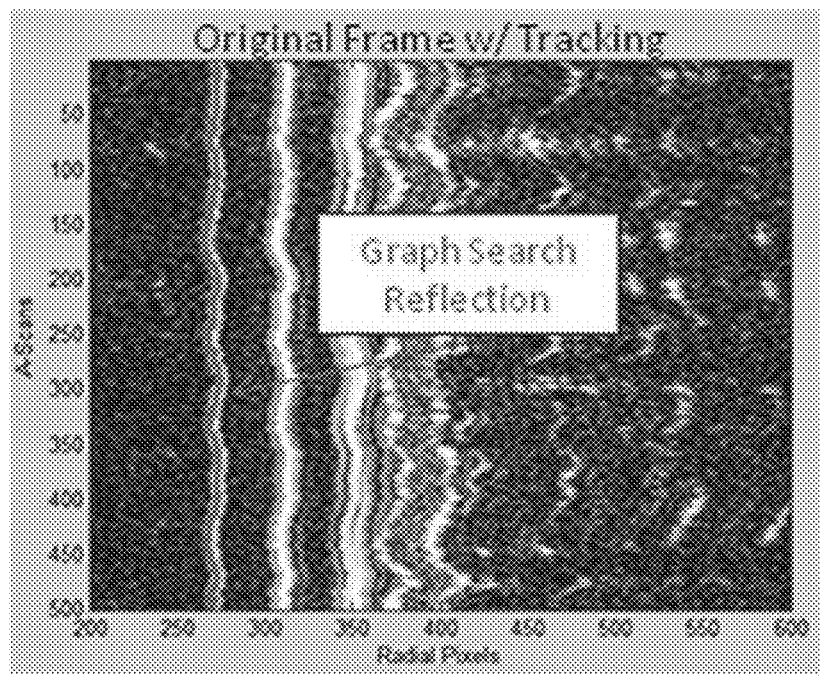
FIGS. 14A-14B are graphs of the second step in the initial lock mode of aligning the reflections across the A-scans in the rectangular image.
Figure 14B:
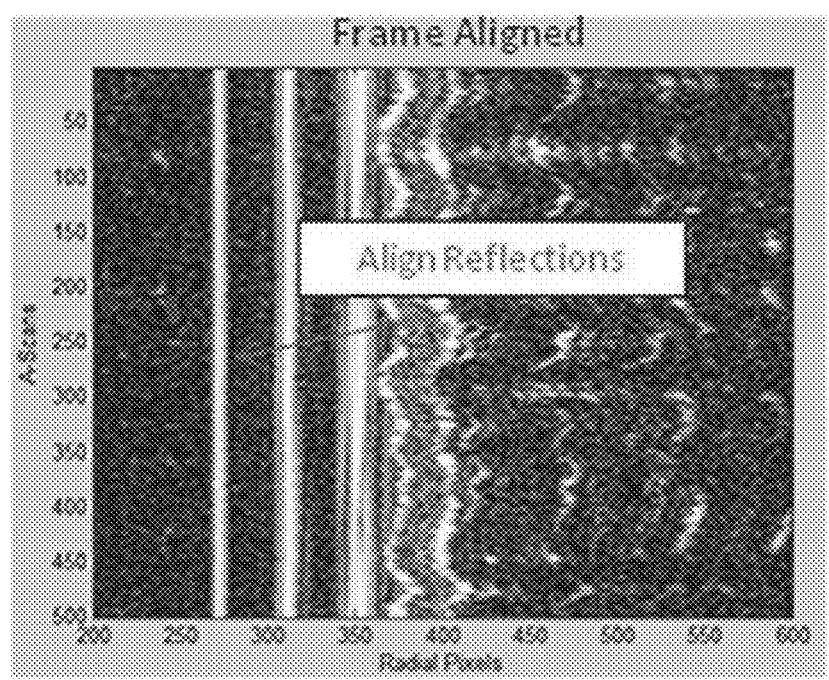

Once the reflections have been centered in the image window the template is computed. The template is an array of pixel numbers versus average amplitude values beginning at the fiber reflection and ending at the lens reflection. The first step in identifying the template is to align the image based on the first strong reflection using a simple graph search algorithm, as shown in FIG. 14A. Aligning the reflections across the A-scans is in the rectangular image is the second step for the initial lock Z-offset calibration mode. Image alignment is done to increase the likelihood reflections are straight in the rectangular image and will be easily identified by their gradients and amplitude, as shown in FIG. 14B. Once the image alignment is complete, the internal catheter reflections are identified using 4 characteristics: (1) Strong X and Weak Y Gradients (Assuming A-Scans Along the Y axis); (2) Consistently High Signal-to-Noise Ratio (SNR) of at least greater than 15 dB; (3) Maximum Distance from First Reflection (Fiber) to Last Reflection (Lens); and (4) Minimum of at least 2 Reflections.

Figure 15A:
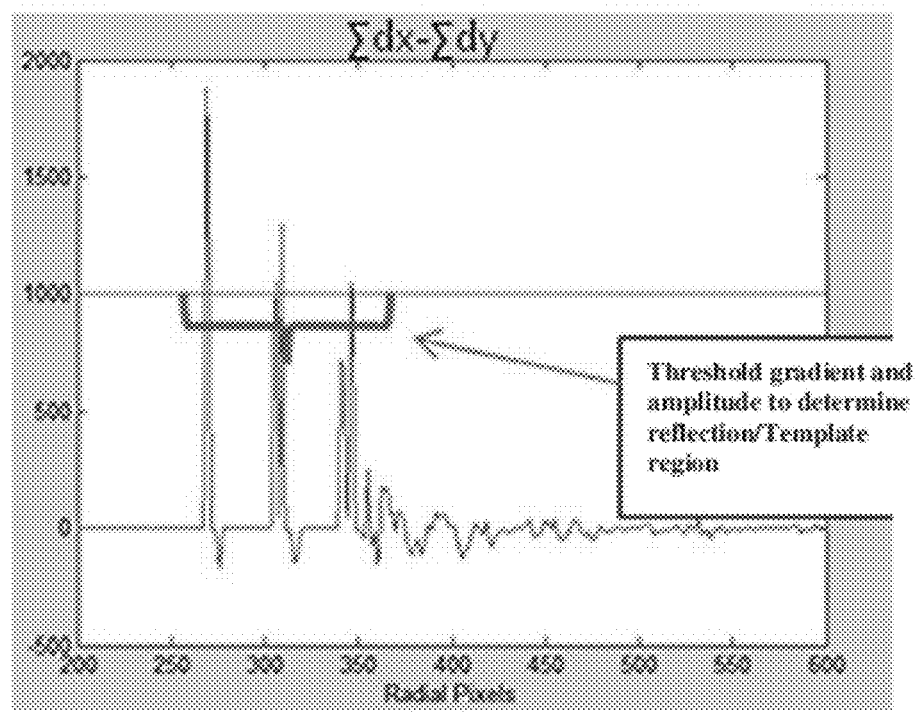
FIGS. 15A-15B are graphs of the third step of identifying the catheter reflections using the gradient and amplitude.
Figure 15B:
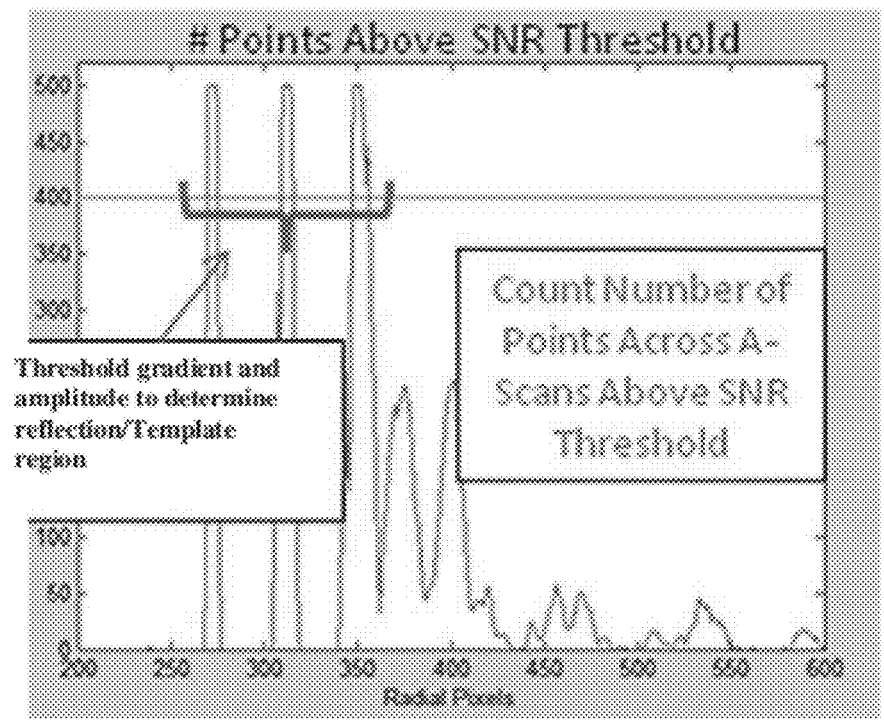
Figure 16A:
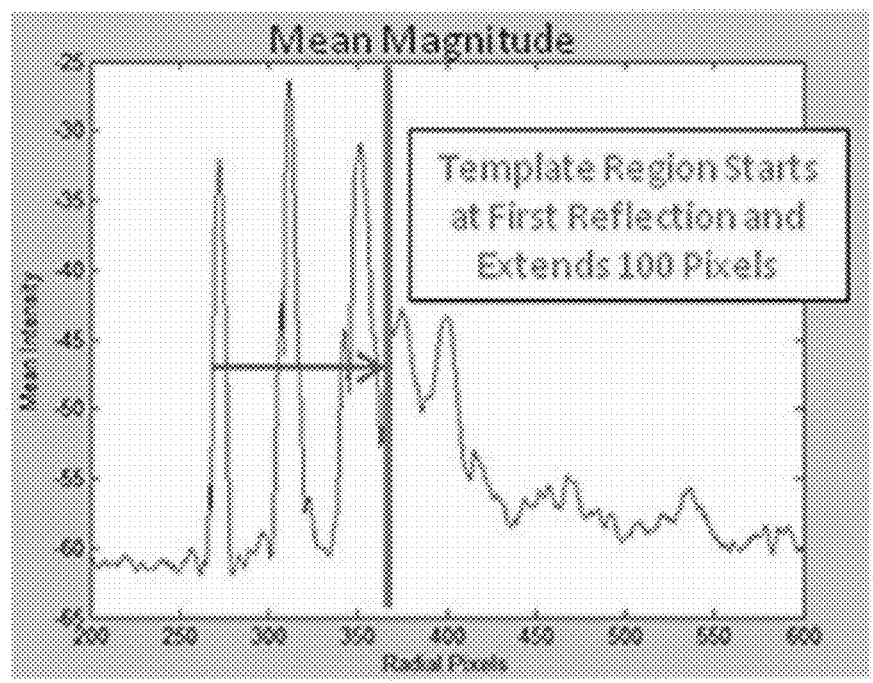
FIGS. 16A-16B are graphs of the fourth step in the initial lock mode of generating the template of reflections and storing for later use.

As shown in FIGS. 15A-15B, the third step in the initial lock mode is to identify the catheter reflections using the X and Y gradients. Step 4 of the initial lock generates template of reflections and stores the template for later use. The template region is then defined as the mean across A-Scans (i.e. angular) starting from the first reflection and ending at the last reflection (with a 5 pixel margin on either side), as shown in FIG. 16A. To prevent small templates due to weak lens reflection, the minimum template size is 100 bins. Alternatively, the minimum template size is at least between about 20 and 1000 bins. Therefore, if the Lens reflection is not detected, the 100 bins after the fiber reflection are selected as the template region. This minimum distance threshold may be determined based on the minimum distance from the fiber to the Inner Diameter (ID) of the sheath. The accuracy of the template is highly dependent on locating the fiber reflection. If the fiber reflection is not found, the template may include the sheath or vessel region and result in improper calibration.

Figure 16B:
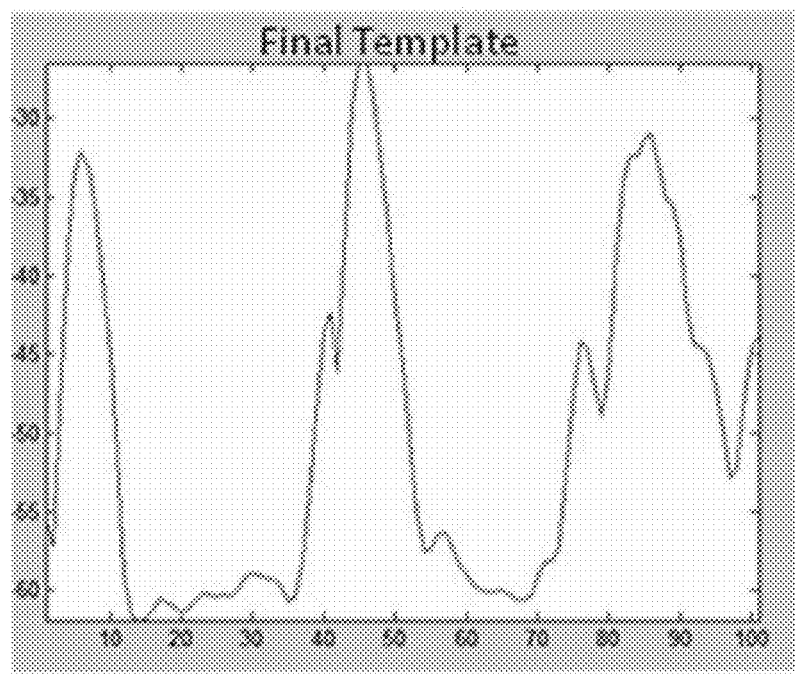
Figure 17:
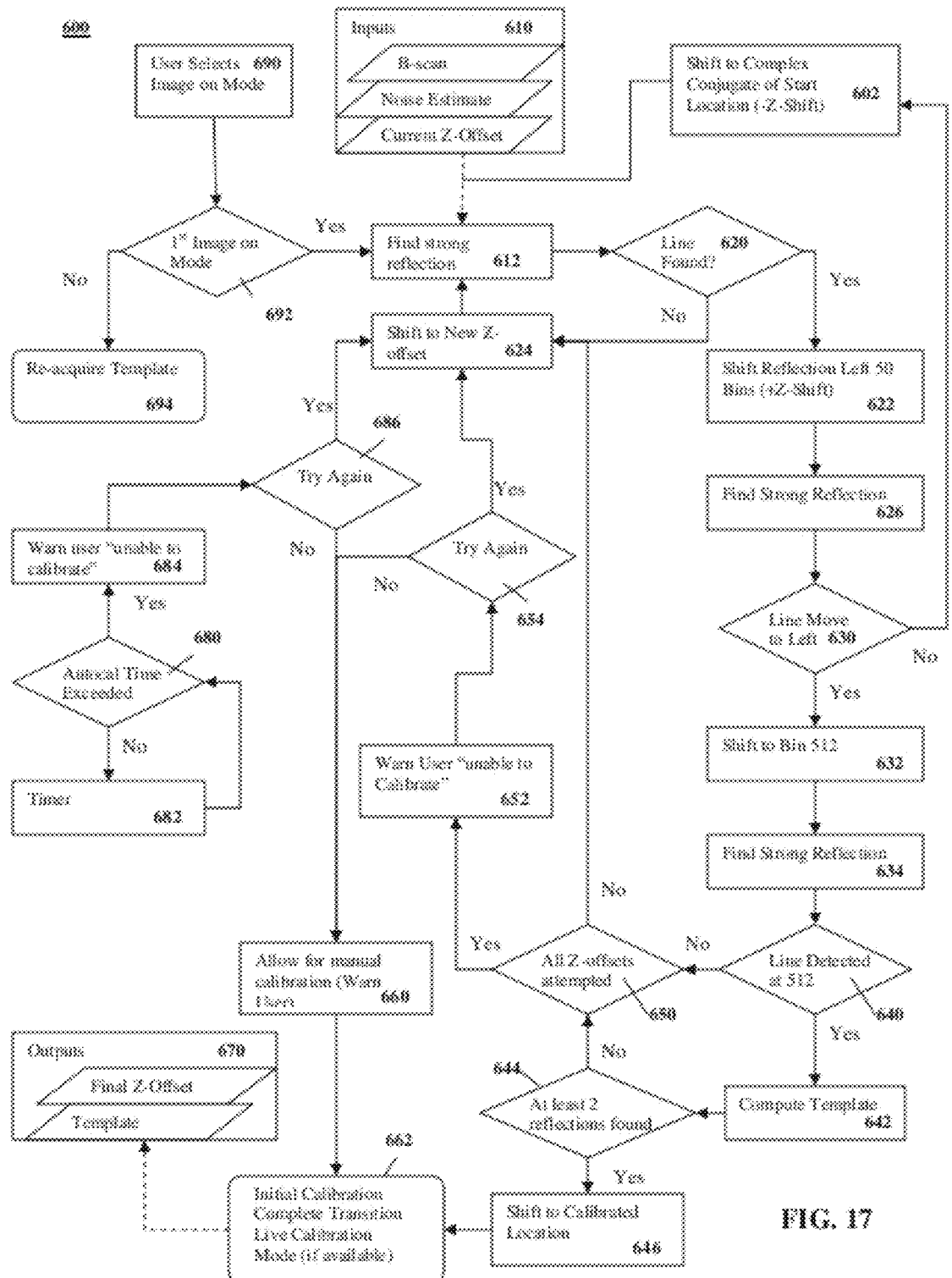
FIG. 17 is flow chart of the Initial Z-Offset Calibration.

As shown in FIG. 16B, once the template is found, it is stored for later use in the subsequent auto-calibration algorithms. The VDL is then shifted to position the fiber reflection at a pre-determined location and the system transitions to live mode. If the reference pattern is not found at this initial VDL position (unlikely but still non-zero probability), the value is assumed to be incorrect and a backup initial estimate search is performed by the system. The backup search procedure sweeps through VDL positions in a pre-determined fashion while the pattern recognition algorithm attempts to lock onto the reference pattern. Entering this backup search procedure is undesirable, because additional time is used to find the correct initial calibration. If the backup search fails (i.e. is unable to lock onto the reference pattern), the system assumes that the catheter or its connection to the PIM is faulty and the user is notified to use an alternate catheter.

FIG. 17 is flow chart of the Initial Lock Z-Offset Calibration method 600. The first step is 690 where the user selects the image on mode. If this is the first image on mode, decision 692, the algorithm proceeds to 612 searching for a strong reflection. Various inputs 610 such as the B-Scan, noise estimate, and current Z-offset may be coupled with step 612. If it is not the first image on mode, the algorithm moves to completion box 694 to reacquire the template by simply shifting the VDL to the position the last template was acquired. After step 612, decision 620 determines if a reflection line has been found. If a reflection has been found, the step 622 proceeds to shift the reflection left n-number of bins for a +Z-shift. In one embodiment, the shift of the reflections may be between about 25 to 100 bins. If the reflection has not been found, then step 624 shifts to a new Z-offset. After step 622, step 626 finds a strong reflection meeting a certain threshold using the mean amplitude or gradient, as indicated previously. Then decision 630 determines if the reflection line move has been to the left. If the reflection line has moved, the step 632 shifts to a particular bin number. If the reflection line has not been moved, then step 602 shifts the VDL to the complex conjugate (CC) of the start location (−Z-shift) to reset to find a strong reflection 612. After step 632, step 634 finds the strong reflection and proceeds to decision 640 to determine if the line has been detected at a particular bin. If the line has been detected at a particular bin, then step 642 computes the template. If the line has not been detected, then decision 650 determines if all the Z-offsets have been attempted. If all the Z-offset have not been attempted, then step 624 shifts to a new Z-offset position and step 612 to find the strong reflection. If all the Z-offsets have been attempted, then step 652 warns the user that the program is unable to calibrate. After step 652, decision 654 warns the user to try again. If the user selects to try again, then step 624 shifts to a new Z-offset and step 612 to find the strong reflection. If the user does not select to try again, then step 660 allows for manual calibration and warns user of manual calibration mode. After step 660, results 662 provides for the initial calibration and complete transition of the live calibration mode. Outputs 670 may be provided for the final Z-offset and the template.

After step 642, decision 644 determines if at least two reflections are found. If at least two reflections are found, step 646 shifts to the calibrated location. If at least two reflections are not found, then decision 650 is attempted to determine if all the Z-offsets have been attempted. In one embodiment, a timer 680 may be coupled with the decision 680 to determine if the autocalibration time has been exceeded. If the autocalibration time has been exceeded, then step 684 warns the user that the program is unable to calibrate. After step 684, decision 686 allows the user to try again. If the user selects to try again, the step 624 shifts to a new Z-offset to find a strong reflection. If the user does not select to try again, the step 660 allows for manual calibration.

In an alternative embodiment of the second mode, a live mode tracking step may be employed. During live mode auto-calibration, the template computed during the initial lock step is utilized to maintain the initial lock calibration position for all frames displayed on the screen on a video monitor or other display device. In one embodiment, the initial lock calibration position for all frames may be at a rate of at least 30 frames-per-second (fps), alternatively, between about 10 to 50 fps. The catheter system may become uncalibrated due to shifts in the optical path length caused by changes in temperature when the catheter is inserted into the body or mechanical strain on the fiber when the catheter is longitudinally pushed or pulled. The live mode algorithm detects the position of the catheter reflections using the template and updates the digital and analog calibration settings to maintain the proper calibration setting. If only a small shift is necessary to maintain the calibration position, a digital shift is applied to the image prior to display. However, if the system becomes significantly un-calibrated or a large shift is necessary to maintain calibration, a Z-offset update is applied (VDL shift).

Figure 20:
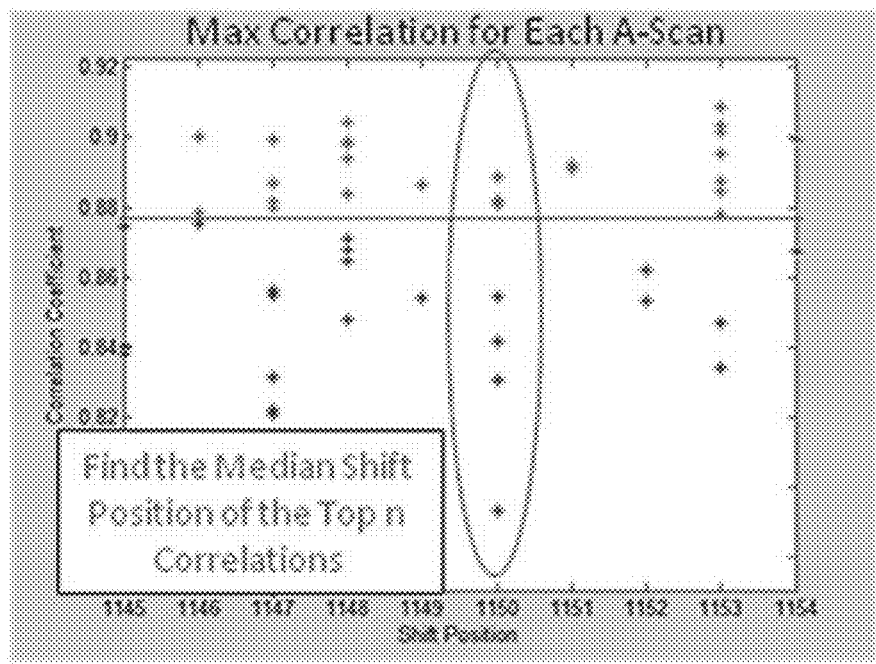
FIG. 20 is a graph of the third step in the live tracking mode for finding the maximum correlation per A-scan and taking the median of the top "n" A-scans.
Figure 21A:
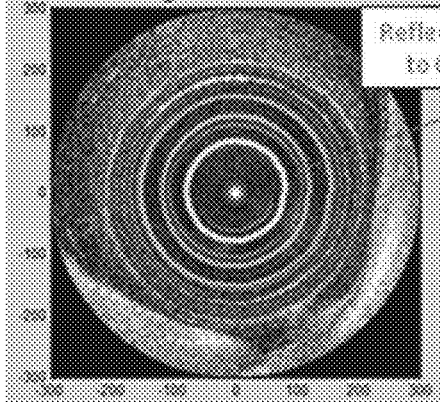
FIGS. 21A-21B are OCT images before and after calibrations in the fourth step by applying the digital shift to the image and scan-convert.
Figure 21B:
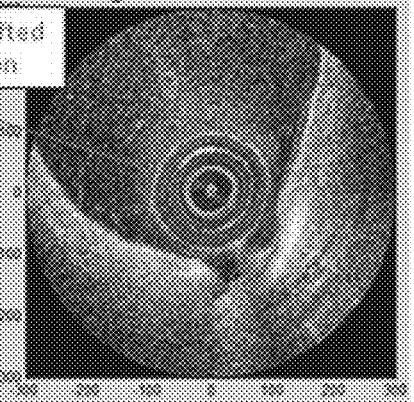

The reflections are identified during live-mode tracking by finding the maximum correlation between the template and A-scans (i.e. template matching). The search region for identifying the reflections is limited based on the maximum expected shift from frame to frame. The template matching algorithm is slightly different than most standard template matching implementations, since it modifies the template based on the search position to account for the wrapped complex conjugate signal. Prior to computing the correlation, the "full template" is generated which includes the mirrored complex conjugate signal, as shown in FIGS. 18A-18D. To compute the full template, first the original template is shifted to a search position, as shown in FIG. 18A, and second the signal is summed with the mirrored version of the same signal, as shown in FIG. 18B. The correlation coefficient of the full template and each A-scan is then computed, as shown in FIG. 19. This process is then repeated for each possible shift position in the search region. Once all correlations have been computed, the position of maximum correlation for each A-scan is found, as shown in FIG. 20. The final reflection position is assigned as the median position of the top "n" correlations. Once the calibration shift is identified, the image is digitally adjusted to return the reflections to their calibrated position, as shown in FIGS. 21A-21B. If the shift is beyond a pre-determine threshold for "n" frames, an update to the Z-offset (VDL) is applied. This algorithm is repeated for every image displayed on a screen in live mode and utilizes the previous frames correlation match and Z-offset to determine the search region for the next frame.

Figure 22:
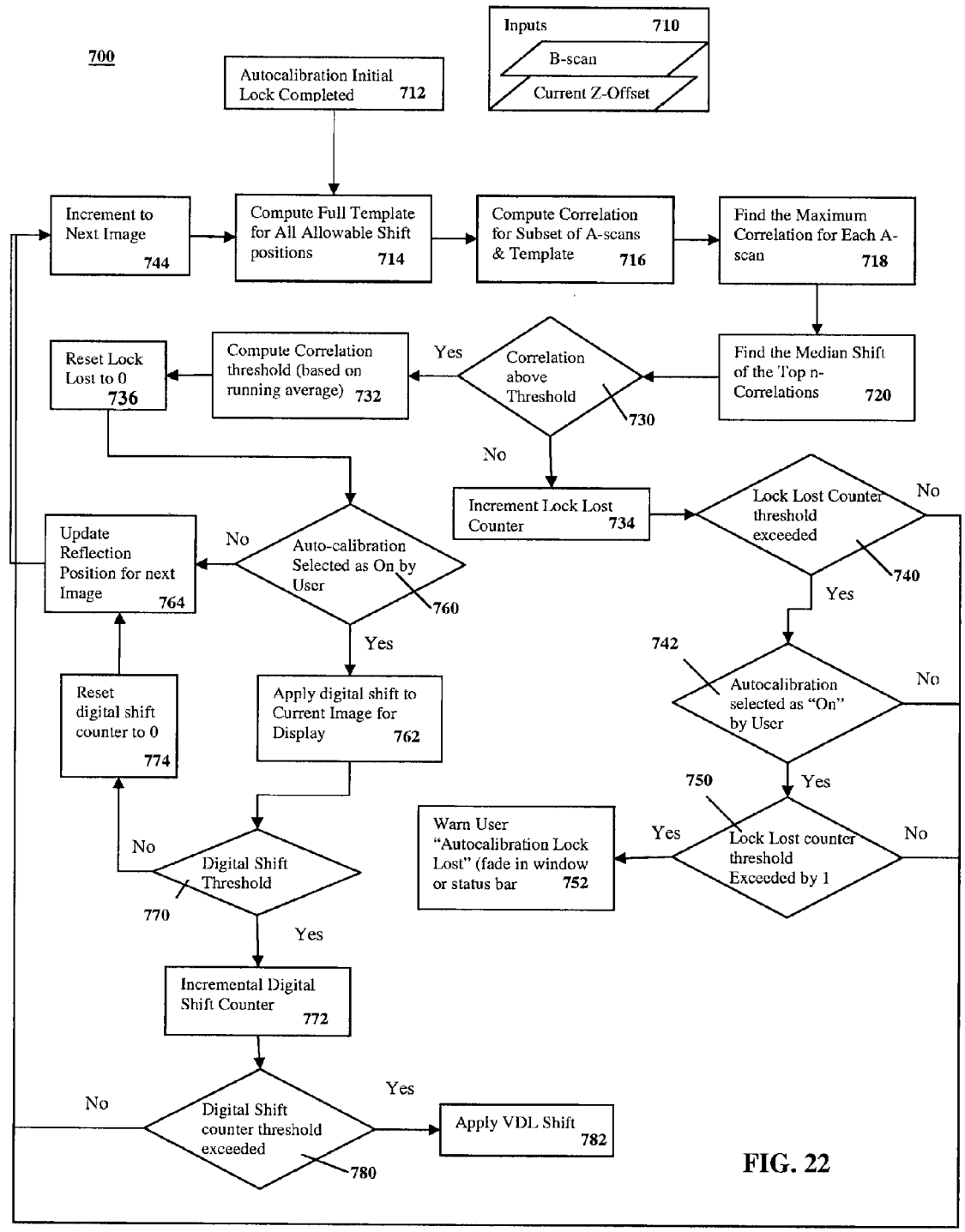
FIG. 22 is a flow chart of the live-mode tracking, in accordance with one embodiment.

FIG. 22 provides a flowchart of the algorithm and the user interaction for the live mode tracking process 700. In the live mode calibration process, the calibration continues until "image off" is selected or a catheter longitudinal pullback is initiated. The position of the reflections just before the pullback begins is stored for use in a Playback Mode autocalibration setting, as described below. Various inputs 710 may be coupled with the live-mode tracking process, such as the B-scan, the current Z-offset, and the like, as previously indicated. Step 712 determines if the autocalibration of the initial lock has been completed. Then step 714 computes the full template for all allowable shift positions. Then step 716 computes the correlation for the subset of A-scans and the template. Then step 718 finds the maximum correlation for each scan. Then step 720 finds the median shift of the top n-correlations. Then decision 730 determines if the correlation is above a particular threshold. If the correlation is above a particular threshold, then step 732 compute the correlation threshold based on the running average. If the correlation is not above a particular threshold, the step 734 incremental lock lost counter proceeds. After step 734, decision 740 determines if the lock lost counter threshold has been exceeded. If the lock lost counter threshold has been exceeded, then decision 742 checks if the user has selected autocalibration as "on" to determine if the user needs to be warned for the error. If the lock lost counter threshold has not been exceeded, then step 744 proceeds to increment to the next image, which is followed by step 714 to compute the full template for all allowable shifts positions for live-mode tracking. In decision 742, if the autocalibration is selected "on" by the user, then decision 750 determines if the lock lost counter threshold is exceeded by 1. If the autocalibration is not selected "on" by the user, the step 744 proceeds to increment to the next image. If the lock lost counter threshold is not exceeded by 1, then step 744 proceeds to increment to the next image. If the lock lost counter threshold is exceeded by 1, then step 752 warns the user that the autocalibration lock was lost, whereby the program can fade in the window or status bar of the computer.

After step 732, step 736 resets the lock lost to 0. Then decision 760 determines if the autocalibration has been selected "on" by the user. If the autocalibration has been selected "on" by the user, then step 762 applies a digital shift to the current image for display. If the autocalibration has not been selected "on" by the user, then step 764 updates the reflection position for the next image. After step 764, step 744 increments the program to the next image. After step 762, decision 770 determines if the digital shift threshold has been met. If the digital shift threshold has been met, the step 772 proceeds with the incremental digital shift counter. If the digital shift threshold has not been met, then step 774 resets the digital shift counter to 0, which then proceeds to step 784 to update the reflection position for the next image. After step 772, decision 780 determines if the digital shift counter threshold has been exceeded. If the digital shift counter threshold has been exceeded, then step 782 applies a VDL shift. If the digital shift counter threshold has not been exceeded, then step 744 increments to the next image for the live mode tracking process. In the live mode calibration process, the calibration continues until "image off" is selected or a catheter longitudinal pullback is initiated. The position of the reflections just before the catheter pullback begins is stored for use in a Playback Mode autocalibration setting, as described below.

Figures 23A, 23B:
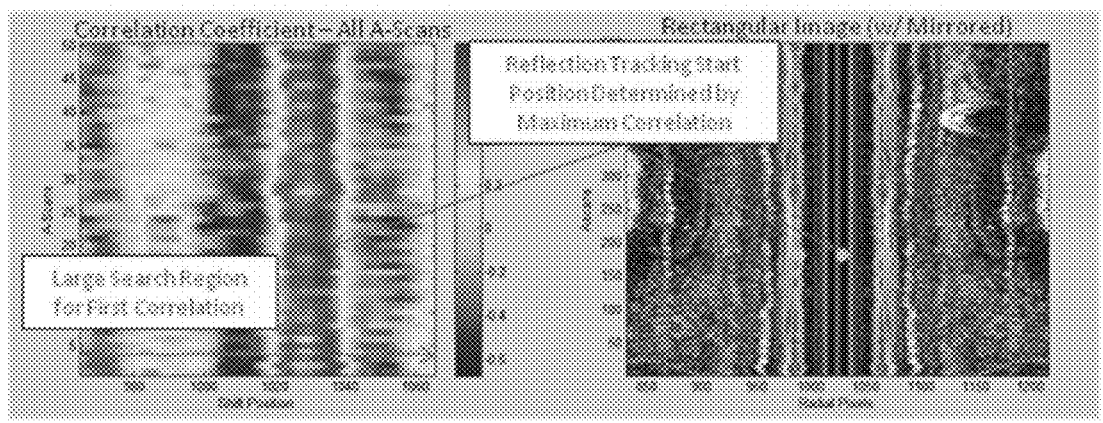
FIGS. 23A-23B are graphs of the first step in the playback tracking mode to determine the starting position of the reflection tracking using maximum correlation across all A-scans with large search region.
Figure 24:
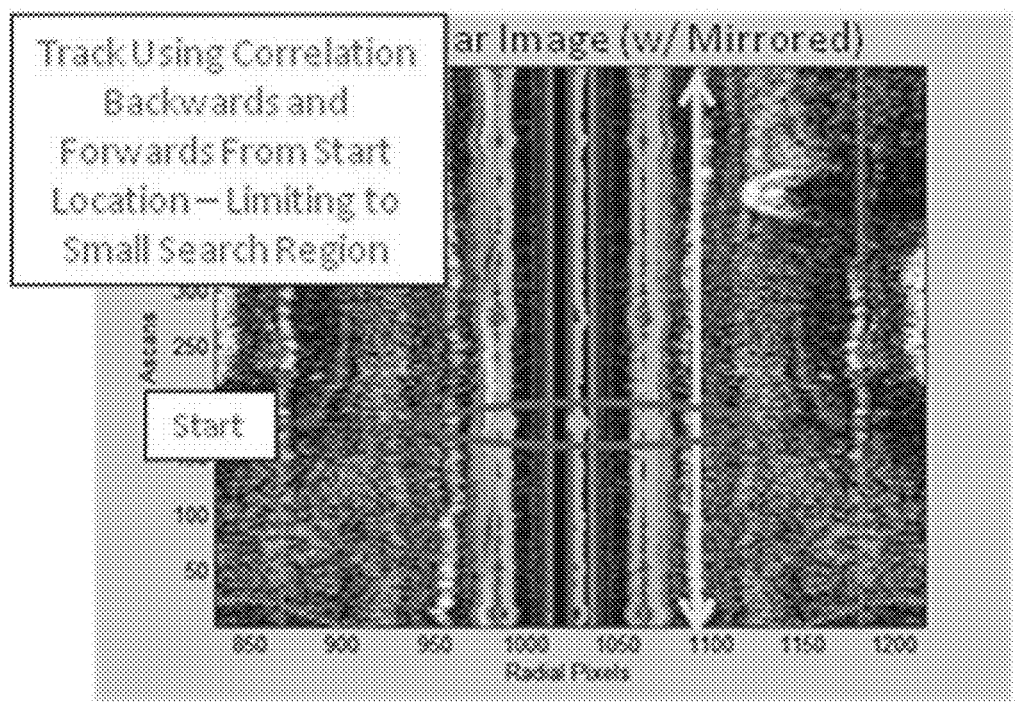
FIG. 24 is a graph of the second step of the playback tracking mode from the starting Position, track reflections backward and forwards A-scan by A-scan using the same correlation technique but with small search region.
Figure 25A:
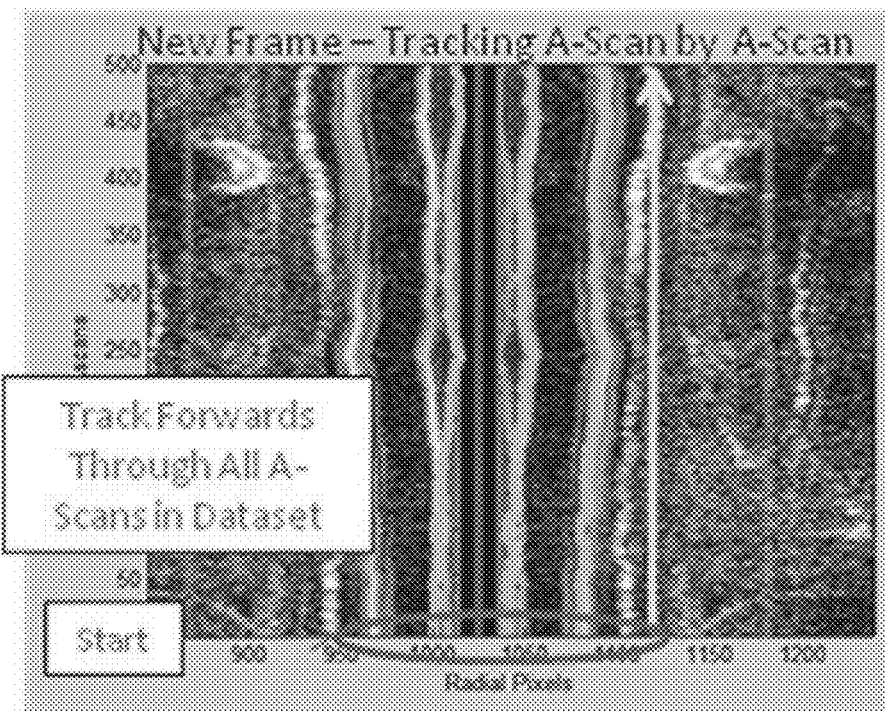
FIGS. 25A-25B are graphs of the third step in the playback tracking mode and continuing to track A-scan by A-scan through all frame in dataset and store reflection position for later alignment and display to a viewer on a video monitor or other physical display device.
Figure 25B:
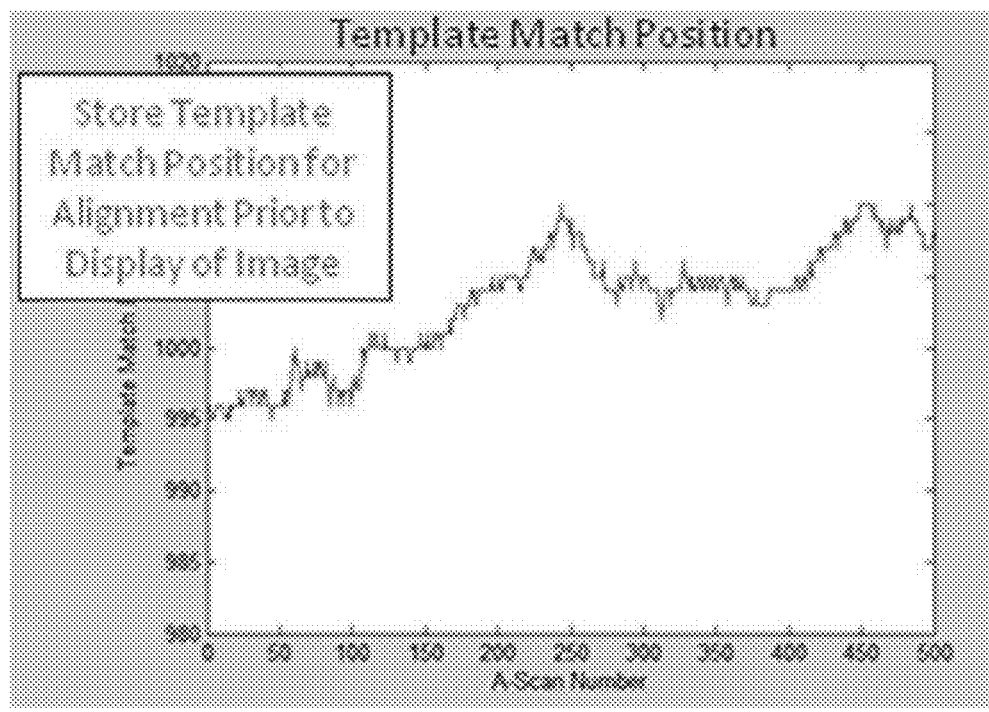

In an alternative embodiment of the third mode, a playback mode tracking occurs after the user has recorded an image dataset. The playback mode tracking performs auto-calibration on every A-scan in the dataset. Similar to live mode tracking, the playback mode utilizes the correlation of the template and image A-scans at limited shift locations to determine the position of the reflections. Identifying the initial position of the reflections is such that the first frame of the dataset is treated different from the other frames. In the first frame of the dataset, the correlations for all allowable shifts and all A-scans are computed to find the maximum correlation, as shown in FIGS. 23A-23B. From the point of the maximum correlation, the algorithm then traces through each A-scan backwards and forwards computing the correlation for each possible shift, as shown in FIG. 24. The allowable shift region for the first search is broad to allow for sudden jumps that may occur during the transition from live mode to playback mode. Once the start position is determined, the A-scan by A-scan search is limited to a small region given that the time and possible movement between A-scans is small relative to the frame to frame motion. For example, for the first frame the search region may be set to −50 to +50 pixels from the last location, once the maximum correlation is found, the search region is limited to −1 to +1 pixels for each A-scan. Alternatively, the search region may be set to at least about −500 to +500 pixels, alternatively between at least about −400 to +400, alternatively between about −300 to +300, and the like. The search region may be limited to between about −10 to +10, alternatively, between about −5 to +5, alternatively between about −0.1 and +0.1. Once the first frame has been fully traced, as shown in FIG. 25A, the algorithm moves on to the next frame beginning with the first A-scan and limited the search region based on the position of the reflection in the last A-scan. FIG. 25B shows that the reflection position is stored for later alignment and display through storing the template match position for alignment prior to the display of the image on a screen of a video monitor or other display device. This is repeated for each A-scan in all frames.

Figure 26:
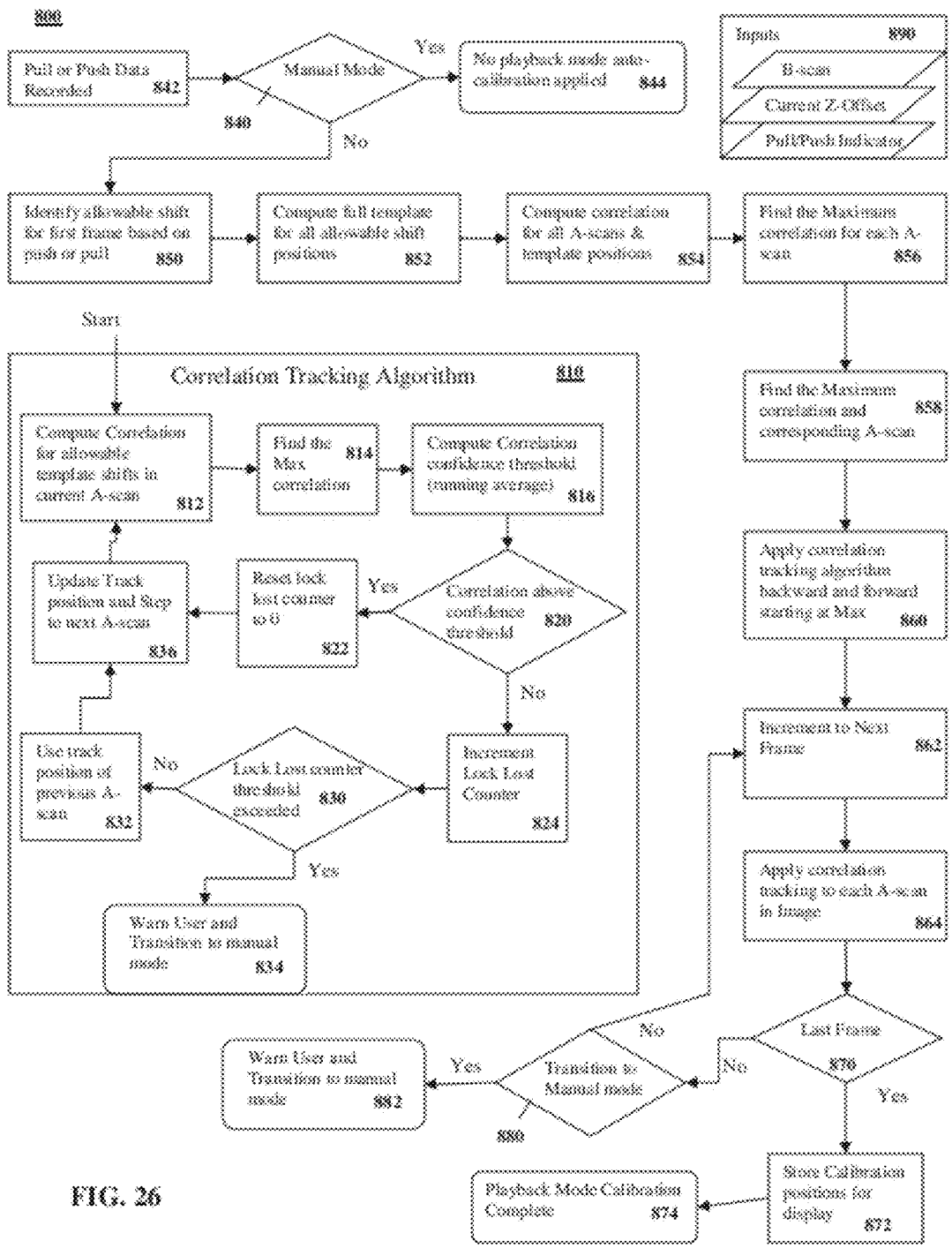
FIG. 26 is a flow chart of the Playback Mode Tracking Algorithm.

The detailed flow chart of the playback mode calibration process 800 is provided in FIG. 26. The playback mode calibration initializes by searching all A-scans within an image to identify the peak correlation. From the peak, the correlation tracker tracks forwards and backwards to identify the reflection position for each A-scan in the first frame. This search is applied to the first frame to guarantee a strong initial lock. Each of the following frames after the first frame is tracked A-scan by A-scan with limited search regions. The manual mode 840 is transitioned when the lock lost counter threshold has been exceeded and the user selects manual mode. Alternatively, the manual mode 840 may be selected if the pull or push data has been recorded 842. If manual mode has been selected, then no playback mode autocalibration will be applied in step 844. If manual mode has not been selected, then step 850 identifies the allowable shifts for the first frame based on the push or pull of the catheter. Then step 852 computes the full template for all allowable shift positions. Then step 854 computes the correlation for all A-scans and template positions. Then step 856 finds the maximum correlation for each A-scan. Then step 858 finds the maximum correlation and corresponding A-scan. Then step 860 applies the correlation tracking algorithm 810 to each A-scan in the image.

The correlation tracking algorithm 810 starts with step 812 of computing the correlation for allowable template shifts in the current A-scan. Then step 814 finds the maximum correlation for that A-scan. Then step 816 computes the correlation confidence threshold of the running average. Then decision 820 determines if the correlation is above a particular confidence threshold. If the correlation is above a particular confidence threshold, then step 822 resets the lock lost counter to 0. If the correlation is not above a particular confidence threshold, then step 824 proceeds to increment the lock lost counter. After step 824, decision 830 determines if the lock lost counter threshold has been exceeded. If the lock lost counter threshold has not been exceeded, the step 832 uses the track position of the previous A-scan. If the lock lost counter threshold has been exceeded, then step 834 it warns the user and transitions to manual mode. Both step 822 and 832 proceed to step 836 to update the track position and steps to the next A-scan. After step 836, step 812 computes the correlation for allowable shifts in the current A-scan.

After step 864 of applying the correlation tracking algorithm to each A-scan in the image, decision 870 determines if it is the last frame. If it is the last frame, then step 872 stores the calibration positions for the display. If there are more frames, then decision 880 determines if the transition to manual mode is required or commanded. If the transition to manual mode has been selected, then step 862 increments to the next frame. If the transition to manual mode has not been selected, then step 882 warns the use and transitions to manual mode. After step 872, step 874 determines that the playback mode calibration has been completed. Various inputs 890 may be coupled with the playback mode process, such as the B-scan, current Z-offset, and the pull or push indicator for the catheter.

Figure 27:
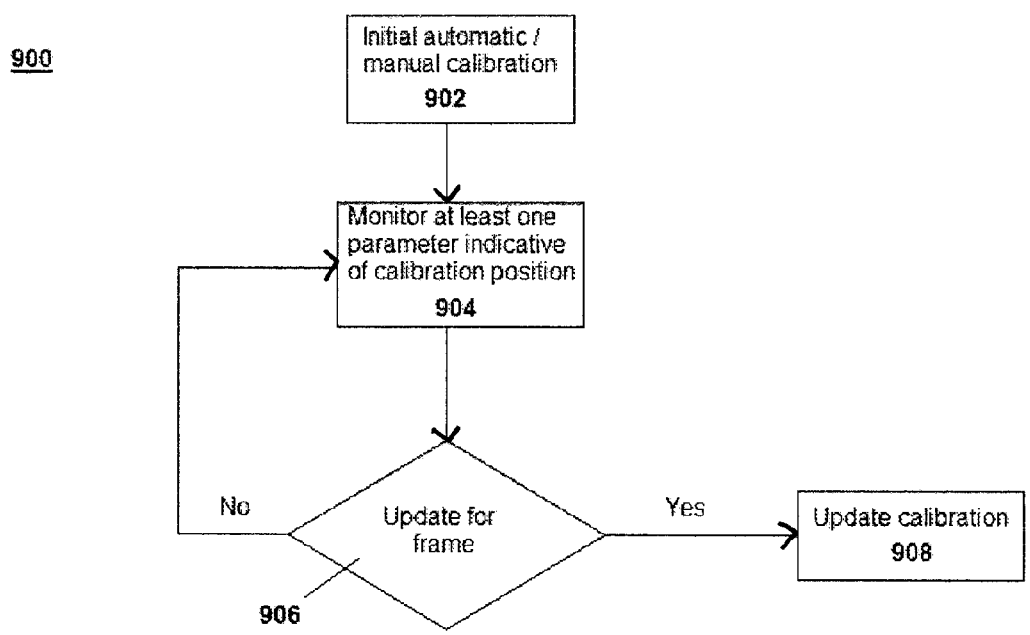
FIG. 27 is a flow chart of one embodiment of the automatic calibration.

Generally, in one embodiment for the auto-calibration 900 is shown in FIG. 27. Any of the previously discussed calibration methods may be used to continuously update and maintain the calibration on a frame-by-frame basis after the initial calibration. Step 902 performs the initial automatic calibration or manual calibration as previously discussed. Step 904 monitors at least one parameter indicative of the calibration position. Decision 906 determines if the calibration needs to be updated on the existing frame or subsequent frame. If the calibration does not need to be updated for the frame, then the automatic calibration continues to monitor the parameter indicative of the calibration position in step 904. If the calibration does need to be updated for the frame, the step 908 automatically updates the calibration (such as to digitally shift the image, apply the z-offset shift, or any of the methods previously discussed. The frame may be an A-scan, or set of frames.

It will be understood that each block of the flowchart illustrations, and combinations of blocks in the flowchart illustrations, as well any portion of the module, systems and methods disclosed herein, can be implemented by computer program instructions. These program instructions may be provided to a processor to produce a machine, such that the instructions, which execute on the processor, create means for implementing the actions specified in the flowchart block or blocks or described for the tissue classifier, imager, control module, systems and methods disclosed herein. The computer program instructions may be executed by a processor to cause a series of operational steps to be performed by the processor to produce a computer implemented process. The computer program instructions may also cause at least some of the operational steps to be performed in parallel. Moreover, some of the steps may also be performed across more than one processor, such as might arise in a multi-processor computer system. In addition, one or more processes may also be performed concurrently with other processes or even in a different sequence than illustrated without departing from the scope or spirit of the invention.

The computer program instructions can be, stored on any suitable computer-readable medium including, but not limited to, RAM, ROM, EEPROM, flash memory or other memory technology, CD-ROM, digital versatile disks (DVD) or other optical storage, magnetic cassettes, magnetic tape, magnetic disk storage or other magnetic storage devices, or any other medium which can be used to store the desired information and which can be accessed by a computing device.

It will be understood that the catheter pullback may be performed by pulling the catheter from a proximal end to a distal end of the region being imaged. It also will be understood that the intravascular imaging techniques described above can also be used with other types of imaging techniques that use a catheter insertable into patient vasculature. For example, the intravascular imaging techniques can be used with any imaging techniques configured and arranged to assess one or more measurable characteristics of patient tissue (e.g., intravascular magnetic resonance imaging, spectroscopy, temperature mapping, or the like).

The systems and methods described herein may be embodied in many different forms and should not be construed as limited to the embodiments set forth herein. Accordingly, the disclosed systems and methods may take the form of an entirely hardware embodiment, an entirely software embodiment, or an embodiment combining software and hardware aspects. The systems and methods of use described herein can be performed using any type of computing device, such as a computer that includes a processor or any combination of computing devices where each device performs at least part of the process or method.

Suitable computing devices typically include mass memory and typically include communication between devices. The mass memory illustrates a type of computer-readable media, namely computer storage media. Computer storage media may include volatile, nonvolatile, removable, and non-removable media implemented in any method or technology for storage of information, such as computer readable instructions, data structures, program modules, or other data. Examples of computer storage media include RAM, ROM, EEPROM, flash memory, or other memory technology, CD-ROM, digital versatile disks (DVD) or other optical storage, magnetic cassettes, magnetic tape, magnetic disk storage or other magnetic storage devices, Radiofrequency Identification tags or chips, or any other medium which can be used to store the desired information and which can be accessed by a computing device. Communication between devices or components of a system can include both wired and wireless (e.g., RF, optical, or infrared) communications.

While the invention has been described in connection with various embodiments, it will be understood that the invention is capable of further modifications. This application is intended to cover any variations, uses, or adaptations of the invention following, in general, the principles of the invention and including such departures from the present disclosure as are within the known and customary practice within the art to which the invention pertains.

What is claimed is:

1. A method of calibrating a catheter, comprising:
   providing a template of catheter reflection lines specific to an optical coherence tomography catheter;
   obtaining an image in the catheter;
   comparing the template to catheter reflection lines of the image; and
   adjusting the Z-offset of the catheter based on the comparison step to align the image catheter reflection lines with the template.

2. The method of claim 1, wherein the template is stored or operably accessible with the catheter.

3. The method of claim 1, wherein the template is derived directly from another image obtained in the catheter.

4. The method of claim 1, wherein the comparing step comprises matching the template with a signal of the image and identifying a peak.

5. The method of claim 4, wherein the image is binary.

6. The method of claim 4, further comprising selecting the peak that corresponds to a strongest template match, the strongest template match representing one of the catheter reflection lines of the image.

7. The method of claim 6, wherein the peak is above a certain value.

8. The method of claim 4, further comprising changing the Z-offset position if the image does not match the template; obtaining a second image in the catheter at the changed Z-offset position; and performing the steps of comparing and adjusting on the second image.

9. The method of claim 1, wherein the adjusting Z-Offset step comprises mechanically shifting a Variable Delay Line.

10. The method of claim 4, wherein the Z-offset is adjusted to align the image catheter reflection lines with the template if an intensity of the peak of the image matches the template.

11. The method of claim 6, wherein the Z-offset is adjusted to align the image catheter reflection lines with the template based on the strongest template match.

* * * * *